United States Patent
Chun et al.

(10) Patent No.: US 9,827,075 B2
(45) Date of Patent: Nov. 28, 2017

(54) DETERMINATION OF A THREE DIMENSIONAL RELATION BETWEEN UPPER AND LOWER JAWS WITH REFERENCE TO A TEMPOROMANDIBULAR JOINT

(71) Applicant: Hankookin, Inc., Raleigh, NC (US)

(72) Inventors: James Jiwen Chun, Raleigh, NC (US); Andrew Youngho Chun, Raleigh, NC (US); Angela Soyoung Chun, Raleigh, NC (US); Jennifer Miseong Chun, Raleigh, NC (US)

(73) Assignee: HANKOOKIN, INC., Raleigh, NC (US)

( * ) Notice: Subject to any disclaimer, the term of this patent is extended or adjusted under 35 U.S.C. 154(b) by 602 days.

(21) Appl. No.: 14/222,499

(22) Filed: Mar. 21, 2014

(65) Prior Publication Data
US 2014/0287379 A1 Sep. 25, 2014

Related U.S. Application Data

(60) Provisional application No. 61/803,907, filed on Mar. 21, 2013, provisional application No. 61/805,157, filed on Mar. 26, 2013, provisional application No. 61/896,769, filed on Oct. 29, 2013.

(51) Int. Cl.
*A61C 9/00* (2006.01)
*A61C 19/05* (2006.01)

(52) U.S. Cl.
CPC ............ *A61C 9/0006* (2013.01); *A61C 19/05* (2013.01)

(58) Field of Classification Search
CPC .............................. A61C 9/0006; A61C 19/05
See application file for complete search history.

(56) References Cited

U.S. PATENT DOCUMENTS

| | | | | | |
|---|---|---|---|---|---|
| 1,517,197 | A | * | 11/1924 | Cuttitta | A61C 9/0006 433/48 |
| 1,652,910 | A | * | 12/1927 | Psayla | A61C 9/0006 433/41 |
| 3,501,837 | A | * | 3/1970 | Clark | A61C 9/0006 433/38 |

(Continued)

*Primary Examiner* — Ralph Lewis
(74) *Attorney, Agent, or Firm* — Ash Tankha; Lipton, Weinberger & Husick

(57) ABSTRACT

An apparatus including a bite frame and a bite shaped member is provided. The bite frame includes one or more arcuate frame elements defining an opening for accommodating a mesh element or the bite shaped member that receives a bite registration material for registering a bite impression. The bite shaped member has a geometrical body structure, upper and lower channels of configurable shapes, and upper and lower windows. The upper and lower windows are separated by a space for receiving and allowing flow of the bite registration material to register a vertical distance between the upper and lower jaws. An image processing system operably connected to the apparatus determines the three-dimensional relation between the upper and lower jaws with reference to temporomandibular joints using panoramic images of the upper and lower jaws, reference points provided by radio-opaque markers, three-dimensional scanned images of the bite impression, and three-dimensional head surface images.

6 Claims, 36 Drawing Sheets

(56) References Cited

U.S. PATENT DOCUMENTS

| | | | | |
|---|---|---|---|---|
| 5,102,335 A | * | 4/1992 | Getz | A61C 9/0006 433/38 |
| 5,513,985 A | * | 5/1996 | Robertson | A61C 9/0006 433/37 |
| 8,821,158 B1 | * | 9/2014 | Hultgren | A61C 9/0006 433/215 |

* cited by examiner

DETERMINATION OF A THREE DIMENSIONAL RELATION BETWEEN UPPER AND LOWER JAWS WITH REFERENCE TO A TEMPOROMANDIBULAR JOINT

CROSS REFERENCE TO RELATED APPLICATIONS

This application claims priority to and the benefit of provisional patent application No. 61/803,907 titled "Determination Of A Three Dimensional Relation Between Upper and Lower Jaws With Reference To A Temporomandibular Joint", filed in the United States Patent and Trademark Office on Mar. 21, 2013; provisional patent application No. 61/805,157 titled "Determination Of A Three Dimensional Relation Between Upper and Lower Jaws With Reference To A Temporomandibular Joint", filed in the United States Patent and Trademark Office on Mar. 26, 2013; and provisional patent application No. 61/896,769 titled "Determination Of A Three Dimensional Relation Between Upper and Lower Jaws With Reference To A Temporomandibular Joint", filed in the United States Patent and Trademark Office on Oct. 29, 2013. The specifications of the above referenced patent applications are incorporated herein by reference in their entirety.

BACKGROUND

Determining a spatial relation between an upper jaw and a lower jaw for edentulous patients and determining a spatial relation between the upper jaw and the lower jaw with reference to their temporomandibular joints (TMJs) are challenging tasks in dentistry. A temporomandibular joint (TMJ) is a hinge joint that connects the lower jaw or mandible to the temporal bone. Typically, in a dental prosthesis, an average TMJ location is used to determine a three-dimensional (3D) relation between the upper jaw and the lower jaw. The 3D relation between the upper jaw and the lower jaw with reference to the TMJs of a patient with natural dentition is utilized in many dental treatments, for example, in an orthodontic treatment, pediatric dentistry, restorative dentistry, and in airway management appliances. During an orthodontic treatment, improper tooth movement may result in displacement of the TMJ. In pediatric dentistry, the positions of the upper jaw and the lower jaw with reference to the TMJs are monitored during development of the upper jaw and the lower jaw. In restorative dentistry comprising, for example, crown restoration, bridge restoration, implant supported restoration, etc., cusp inclinations of prosthetic teeth are determined by the location of the TMJs with reference to the upper jaw and the lower jaw. In an air way management treatment, the advancement of the lower jaw is considered along with the 3D location of the TMJ to avoid TMJ displacement.

In an edentulous patient, after a clinical impression of an upper ridge of the upper jaw and a lower ridge of the lower jaw is taken, a customized bite rim has to be fabricated to determine the relation between the upper jaw and the lower jaw. In the case of partially edentulous patients, there is a need for a customized bite shaped member for accurately determining locations where teeth are missing and also for determining the relation between the upper jaw and the lower jaw. The size of the oral cavity of the mouth differs from person to person and careful considerations must be given in order to estimate a vertical distance between the upper jaw and the lower jaw. Therefore, there is a need for different types of bite frames and mesh elements or bite shaped members of configurable shapes with channels separated by different vertical distances for receiving a bite registration material for registering a bite impression and thereafter determining a relation between the patient's temporomandibular joints (TMJs) and the upper jaw and the lower jaw.

Conventional procedures for determining three-dimensional (3D) information of the upper jaw, the lower jaw, and the temporomandibular joints (TMJs) comprise, for example, obtaining an intra oral impression of a coronal portion of the teeth, capturing tomographic images of the upper jaw, the lower jaw, and the TMJs at a focal point from a panoramic X-ray, etc. There is a need for accurately determining the 3D relation between the TMJs and the upper jaw and the lower jaw using the 3D information. In dental panoramic images, most of the distortion, magnification, and minimization are in the horizontal dimension, while the vertical dimension remains accurate. Therefore, there is a need for correcting the horizontal dimensions according to reliable markers to allow the use of panoramic images of the upper jaw, the lower jaw, and the TMJs of the patient for identifying the accurate locations of the upper jaw and the lower jaw with reference to the TMJs.

Hence, there is a long felt but unresolved need for a bite registration apparatus comprising a bite frame and a mesh element or a bite shaped member of configurable shapes with channels separated by different vertical distances for registering a bite impression in edentulous patients and partially edentulous patients, while considering vertical distances between the upper jaw and the lower jaw. Furthermore, there is a need for a method that employs the bit registration apparatus and an image processing system to determine a three-dimensional (3D) relation between the upper jaw and the lower jaw of a patient with reference to the patient's temporomandibular joints (TMJs) using 2D and 3D panoramic X-ray images, 3D scanned images, and 3D head surface images.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The bite registration apparatus disclosed herein addresses the above stated needs for registering a bite impression in edentulous patients and partially edentulous patients, while considering vertical distances between an upper jaw and a lower jaw. The bite registration apparatus disclosed herein comprises a bite frame and a bite shaped member for enabling determination of a three-dimensional (3D) relation between an upper jaw and a lower jaw of, for example, for an edentulous patient. As used herein, "bite frame" refers to a frame configured to receive a bite registration material for registering an impression of an upper jaw, a lower jaw, an upper ridge, and a lower ridge of a patient. The bite frame for enabling determination of a 3D relation between the upper jaw and the lower jaw of an edentulous patient comprises a handle and an arcuate frame element rigidly connected to an upper end of the handle. In an embodiment, the arcuate frame element of the bite frame is an arcuate closed loop frame element. The arcuate frame element defines a generally narrow hollow arcuate opening for accommodating the bite shaped member of one of multiple geometric shapes.

In an embodiment, the bite frame further comprises radio-opaque markers positioned at predetermined locations along an inner rim of the arcuate frame element. The radio-opaque markers provide reference points to positions of the upper jaw and the lower jaw in two-dimensional (2D) panoramic X-ray images of the upper jaw and the lower jaw, a three-dimensional (3D) panoramic X-ray image created using the 2D panoramic X-ray images of the upper jaw and the lower jaw, and 3D scanned images of the bite impression for the determination of the 3D relation between the upper jaw and the lower jaw. In an embodiment, external radio-opaque markers are placed below a patient's ears near the temporomandibular joint (TMJ) area. Reference points to the TMJs of the patient provided by these external radio-opaque markers are recorded in the panoramic X-ray images and are registered to 3D head surface images of the patient's head structure, in which the TMJ reference points provided by external radio-opaque markers are also recorded. In an embodiment, orientation bars are positioned on each of the radio-opaque markers. The orientation bars extend outwardly from each of the radio-opaque markers. The orientation bars facilitate calculation of a 3D orientation of each radio-opaque marker in a projected image of each radio-opaque marker. The projected images are recorded in the 2D and 3D panoramic X-ray images.

In an embodiment, another bite frame is used for enabling determination of a three-dimensional (3D) relation between an upper jaw and a lower jaw of a patient with natural dentition. In this embodiment, the bite frame comprises a handle, an outer arcuate frame element, an inner arcuate frame element, and a mesh element. The outer arcuate frame element is rigidly connected to an upper end of the handle. The inner arcuate frame element is positioned at a predetermined distance from the outer arcuate frame element. The inner arcuate frame element and the outer arcuate frame element are configured to define a generally wide arcuate opening therebetween for mounting the mesh element. The mesh element is configured to receive a bite registration material for registering a bite impression comprising an impression of the upper jaw and an impression of the lower jaw, and thereafter enabling the determination of the 3D relation between the upper jaw and the lower jaw. In an embodiment, the bite frame is configured to form an occlusion curve.

The bite shaped member of the bite registration apparatus disclosed herein is configured to be accommodated within the arcuate opening of the bite frame for enabling determination of a three-dimensional (3D) relation between an upper jaw and a lower jaw of a patient. The bite shaped member disclosed herein comprises a body structure, an upper channel, a lower channel, upper windows, and lower windows. The body structure has an upper surface and a lower surface separated by a mid-section. The upper surface of the body structure is configured to conform to the upper jaw. The lower surface of the body structure is configured to conform to the lower jaw. The body structure is configured in one of multiple flexible geometric shapes. The flexible geometric shapes comprise, for example, a generally arcuate shape, a generally cylindrical shape, a generally tubular shape, a generally trefoil shape, a generally polygonal shape, a generally cuboidal shape, a generally polyform shape, a generally quatrefoil shape, etc. The upper channel is of a configurable shape and is defined on the upper surface of the body structure. The upper channel is configured to receive a bite registration material and engage an upper ridge of the upper jaw to register an impression of the upper ridge of the upper jaw. The lower channel is of a configurable shape and is defined on a lower surface of the body structure. The lower channel is configured to receive a bite registration material and engage a lower ridge of the lower jaw to register an impression of the lower ridge of the lower jaw. The configurable shape of each of the upper channel and the lower channel of the bite shaped member is, for example, one of a generally V shape, a generally rectangular shape, a generally arcuate shape, a generally cuboidal shape, a generally hemispherical shape, a generally elliptical shape, a generally trapezoidal shape, a generally cylindrical shape, a generally tubular shape, etc., or any combination thereof.

The upper windows and the lower windows of the bite shaped member are, for example, rectangular shaped windows. The upper windows are positioned along the upper channel on the upper surface of the body structure. The lower windows are positioned along the lower channel on the lower surface of the body structure. The upper windows and the lower windows are separated by a space therebetween, within the bite shaped member. The space is configured to receive the bite registration material from the upper channel and the lower channel through the upper windows and the lower windows respectively. The upper windows, in fluid communication with the lower windows, allow flow of the received bite registration material from the upper channel to the lower channel to register a vertical distance between the upper ridge of the upper jaw and the lower ridge of the lower jaw for determining the three-dimensional (3D) relation between the upper jaw and the lower jaw. In an embodiment, the bite shaped member further comprises supplementary windows, for example, of a rectangular shape positioned at configurable locations along the mid-section of the body structure. The supplementary windows are in fluid communication with the space between the upper channel and the lower channel of the bite shaped member to allow excess bite registration material to flow out from the space. The registration of the impression of the upper ridge of the upper jaw and the impression of the lower ridge of the lower jaw that constitute the bite impression enable the determination of the three-dimensional (3D) relation between the upper jaw and the lower jaw.

In an embodiment, the bite shaped member is formed of a flexible porous material configurable for changing a shape and a form of the bite shaped member for folding and accommodating the bite shaped member into the arcuate opening of the arcuate frame element of the bite frame. The flexible porous material is configured to absorb the bite registration material. In an embodiment, partial features of the bite shaped member, for example, the upper channel and/or the lower channel, and/or a partial portion of the bite shaped member can be used to form a flexible bite shaped member. These partial features are configurable for creating different flexible bite shaped members. A partial portion of the bite shaped member is configured to register a portion of the upper jaw and the lower jaw, for example, for creating a partial removable prosthesis, or restoring a dental crown, or restoring a dental bridge.

In an embodiment, the bite shaped member comprises a body structure of a generally multi-geometric shape having an upper section and a lower section separated by a mid-section, an upper channel, a lower channel, upper windows, lower windows, and in an embodiment, supplementary windows as disclosed above. In this embodiment, the upper channel and the lower channel of the bite shaped member are, for example, of a rectangular shape. The upper section of the body structure is configured to conform to the upper jaw. The lower section of the body structure is configured to conform to the lower jaw. The upper channel is defined on the upper section of the body structure and is configured to receive a bite registration material and engage an upper ridge of the upper jaw to register an impression of the upper ridge of the upper jaw. The lower channel is defined on the lower section of the body structure and is configured to receive a bite registration material and engage a lower ridge of the lower jaw to register an impression of the lower ridge of the lower jaw. The registration of the impression of the upper ridge of the upper jaw and the impression of the lower ridge of the lower jaw that constitute the bite impression enables determination of the three-dimensional (3D) relation between the upper jaw and the lower jaw. The upper windows are positioned along the upper channel on the upper section of the body structure. The lower windows are positioned along the lower channel on the lower section of the body structure. The upper windows, in fluid communication with the lower windows, allow flow of the received bite registration material from the upper channel to the lower channel to register a vertical distance between the upper ridge of the upper jaw and the lower ridge of the lower jaw for determining the three-dimensional (3D) relation between the upper jaw and the lower jaw. In this embodiment, the bite shaped member further comprises multiple grooves of, for example, a V-shape, positioned at configurable locations on an opposing side wall of the body structure. The grooves are configured to facilitate folding and accommodation of the bite shaped member into the arcuate opening of the arcuate frame element of the bite frame.

In another embodiment, the bite shaped member comprises an elongate body structure and generally V-shaped channels. The elongate body structure has opposing surfaces. The elongate body structure comprises opposing distal end portions configured in multiple shapes to conform to oral cavities of different sizes. The V-shaped channels are configured on the opposing surfaces of the elongate body structure as upper V-shaped channels and lower V-shaped channels. The upper V-shaped channels and the lower V-shaped channels are separated by different vertical distances from each other. The V-shaped channels are configured to interchangeably engage the upper ridge of the upper jaw and the lower ridge of the lower jaw. The V-shaped channels are also configured to receive the bite registration material for registering a bite impression comprising an impression of the upper ridge of the upper jaw and an impression of the lower ridge of the lower jaw, and thereafter enabling determination of the 3D relation between the upper jaw and the lower jaw. In this embodiment, the bite shaped member is further configured to be interchangeably positioned in different directions to enable vertical distance adjustments of the bite shaped member for the registration of the bite impression. In an embodiment, an opening extending between an upper V-shaped channel and a lower V-shaped channel is configured to allow a closer biting distance between upper teeth on the upper jaw and lower teeth on the lower jaw. In another embodiment, a partial portion of the elongate body structure can be cut out and configured to register a portion of the upper jaw and the lower jaw, for example, for creating a partial removable prosthesis, restoring a dental crown, restoring a dental bridge, etc.

The bite shaped members disclosed above are formed of a flexible porous material with a generally low pore per inch (PPI) value to allow enhanced penetration of the bite registration material into the upper channel and the lower channel of the bite shaped member for the registration of the impressions of the upper ridge of the upper jaw and the lower ridge of the lower jaw. As used herein, "pore per inch" indicates cell count of the flexible porous material, that is, the number of cells in the flexible porous material per running inch of the flexible porous material.

Also, disclosed herein is a method that employs the bite registration apparatus and an image processing system for determining a three-dimensional (3D) relation between an upper jaw and a lower jaw of a patient with reference to the patient's temporomandibular joints (TMJs) using dental 2D and 3D panoramic X-ray images, 3D scanned images, and 3D head surface images. The bite registration apparatus comprising the bite frame and the bite shaped member of one of multiple flexible geometric shapes is provided for registering a bite impression. The bite frame comprises first radio-opaque markers for providing first reference points to positions of the upper jaw and the lower jaw. The bite shaped member is inserted into the arcuate opening of the bite frame. A bite registration material is applied into the upper channel and the lower channel of the inserted bite shaped member. The bite frame with the inserted bite shaped member and the applied bite registration material is inserted into the patient's mouth, and aligned with the upper jaw and the lower jaw via a panoramic front guide. Second radio-opaque markers, that is, external radio-opaque markers are positioned proximal to the temporomandibular joints below the patient's ears. The second radio-opaque markers provide second reference points to the temporomandibular joints.

After a bite impression is manually registered, image capture and computer implemented image processing takes place to determine the three-dimensional (3D) relation between the upper jaw and the lower jaw of the patient. The registration of the bite impression enables a dental practitioner to optimally determine the 3D relation after image processing. A panoramic machine operably connected to the panoramic front guide captures two-dimensional (2D) panoramic X-ray images of the upper jaw and the lower jaw with the inserted bite frame. The captured 2D panoramic X-ray images of the upper jaw and the lower jaw with the inserted bite frame contain positions of the upper jaw and the lower jaw identified by the first reference points provided by the first radio-opaque markers of the inserted bite frame, and locations of the temporomandibular joints identified by the second reference points provided by the second radio-opaque markers. The panoramic machine creates a three-dimensional (3D) panoramic X-ray image using the captured 2D panoramic X-ray images of the upper jaw and the lower jaw with the inserted bite frame, by placing the captured 2D panoramic X-ray images of the upper jaw and the lower jaw with the inserted bite frame in a focal plane of the panoramic machine. The 3D panoramic X-ray images are created by curving the 2D panoramic X-ray images along a 3D focal plane of the panoramic machine. The created 3D panoramic X-ray image contains the positions of the upper jaw and the lower jaw identified by the first reference points and the locations of the temporomandibular joints identified by the second reference points.

The image processing system operably connected to the panoramic machine receives the created three-dimensional panoramic X-ray image. The image processing system comprises at least one processor configured to process the created three-dimensional (3D) panoramic X-ray image The image processing system receives 3D scanned images of the bite impression formed using the impression of the upper ridge of the upper jaw and the impression of the lower ridge of the lower jaw from a 3D scanner operably connected to the image processing system. The 3D scanned images comprise the positions of the upper jaw and the lower jaw identified by third reference points provided by the first radio-opaque markers of the inserted bite frame. The image processing system modifies horizontal dimensions of the created 3D panoramic X-ray image by matching the first reference points on the created 3D panoramic X-ray image with the third reference points on the 3D scanned images of the bite impression. The image processing system determines the 3D relation between the upper jaw and the lower jaw with reference to the patient's temporomandibular joints using the received 3D scanned images and the created 3D panoramic X-ray image with the modified horizontal dimensions.

In an embodiment, the image processing system further receives two-dimensional (2D) surface images of the patient's head structure, herein referred to as the "2D head surface images". The 2D head surface images comprise the locations of the temporomandibular joints identified by fourth reference points provided by the second radio-opaque markers. The image processing system constructs a three-dimensional (3D) head surface image comprising images of the upper jaw, the lower jaw, and the temporomandibular joints using the received 2D head surface images. The image processing system matches the fourth reference points on the constructed 3D head surface image with the second reference points on the created 3D panoramic X-ray image for checking and confirming the locations of the temporomandibular joints for verifying the 3D relation between the upper jaw and the lower jaw with reference to the temporomandibular joints. In a 3D space, the 3D panoramic X-ray image of the upper jaw and the lower jaw is placed inside the intra oral region of the 3D head surface image by registering the 3D panoramic X-ray image with both the 3D scanned images of the bite impression through the radio-opaque markers positioned in the bite frame, and the 3D head surface image through the external or second radio-opaque markers.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific structures and methods disclosed herein. The description of a structure or a method step referenced by a numeral in a drawing carries over to the description of that structure or method step shown by that same numeral in any subsequent drawing herein.

DETAILED DESCRIPTION OF THE INVENTION

Figure 1A:
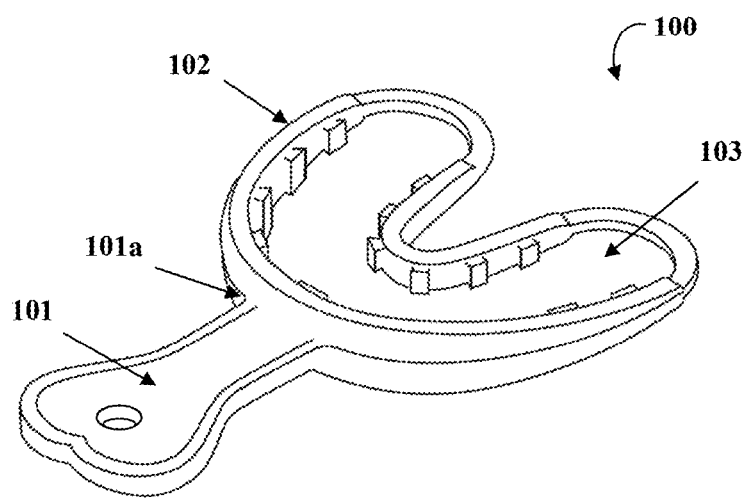
FIG. 1A exemplarily illustrates a top perspective view of a bite frame for enabling determination of a three-dimensional relation between an upper jaw and a lower jaw of an edentulous patient.
Figure 1B:
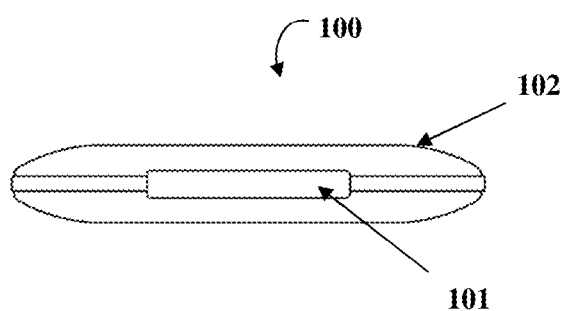
FIG. 1B exemplarily illustrates a front elevation view of the bite frame.
Figure 1C:
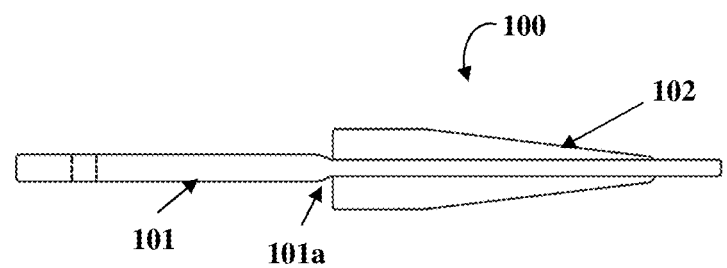
FIG. 1C exemplarily illustrates a side elevation view of the bite frame.
Figure 1D:
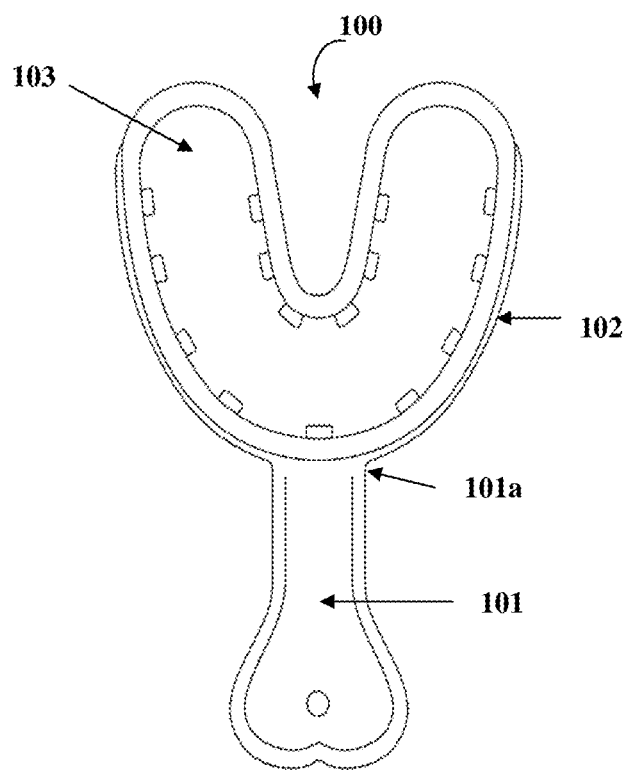
FIG. 1D exemplarily illustrates a top plan view of the bite frame.

FIGS. 1A-1D exemplarily illustrate different views of a bite frame 100 for enabling determination of a three-dimensional (3D) relation between an upper jaw and a lower jaw of an edentulous patient. As used herein, "bite frame" refers to a frame configured to receive a bite registration material for registering an impression of an upper jaw, a lower jaw, an upper ridge, and a lower ridge of a patient. The bite registration material is a dental impression material used for recording or registering a dental impression, for example, an impression of a patient's upper jaw, lower jaw, upper ridge, lower ridge, etc. FIG. 1A exemplarily illustrates a top perspective view of the bite frame 100. FIG. 1B exemplarily illustrates a front elevation view of the bite frame 100. FIG. 1C exemplarily illustrates a side elevation view of the bite frame 100. FIG. 1D exemplarily illustrates a top plan view of the bite frame 100. The bite frame 100 for the edentulous patient comprises a handle 101 and an arcuate frame element 102 rigidly connected to an upper end 101a of the handle 101. The arcuate frame element 102 of the bite frame 100 is an arcuate closed loop frame element. The arcuate frame element 102 defines a generally narrow hollow arcuate opening 103 for accommodating a bite shaped member 500, 700, or 900 exemplarily illustrated in FIGS. 5A-5D, FIGS. 7A-7E, and FIGS. 9A-9H respectively. The bite shaped member 500, 700, or 900 is rigidly attached or glued to the arcuate frame element 102.

Figure 2A:
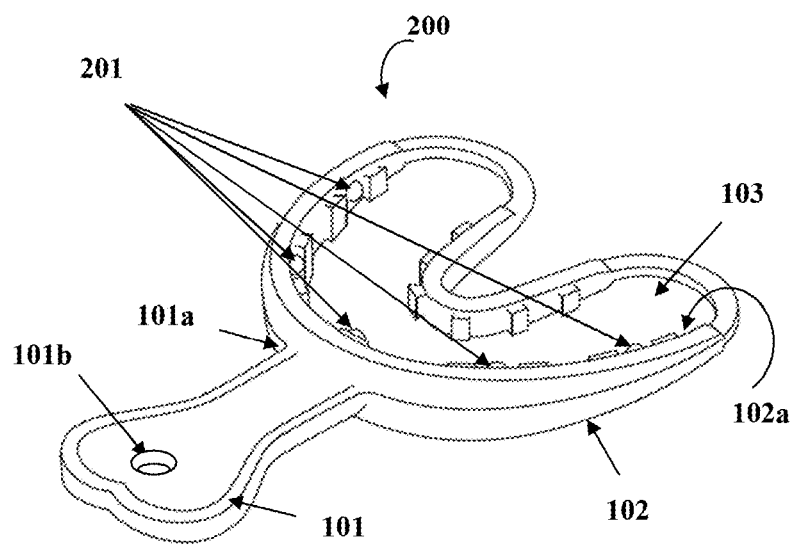
FIG. 2A exemplarily illustrates a top perspective view of an embodiment of the bite frame for enabling determination of a three-dimensional relation between an upper jaw and a lower jaw of an edentulous patient.
Figure 2B:
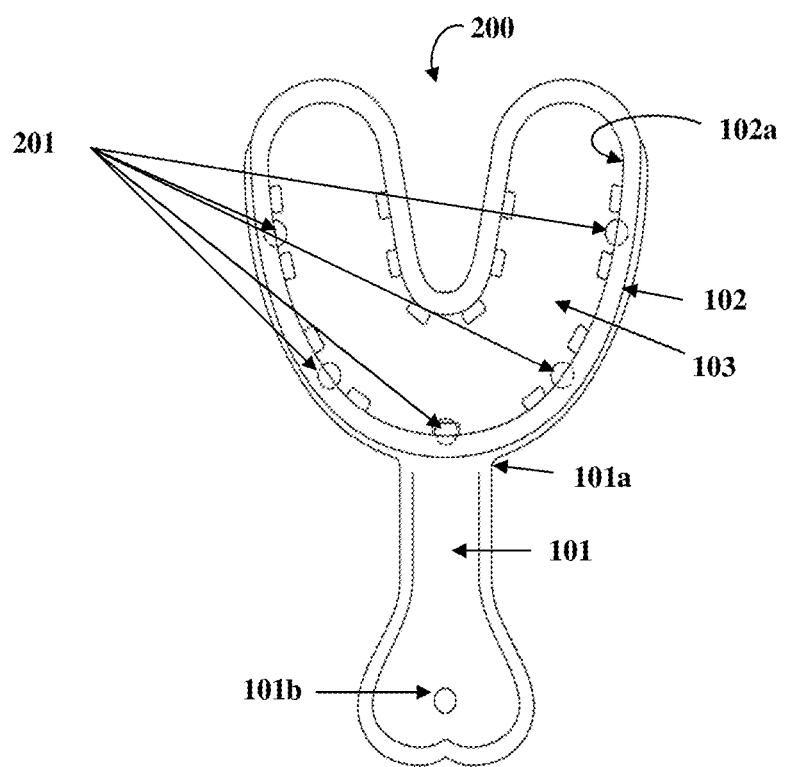
FIG. 2B exemplarily illustrates a top plan view of the embodiment of the bite frame shown in FIG. 2A.

FIGS. 2A-2B exemplarily illustrate different views of an embodiment of the bite frame 100 exemplarily illustrated in FIGS. 1A-1D, for enabling determination of a three-dimensional (3D) relation between an upper jaw and a lower jaw of an edentulous patient. FIG. 2A exemplarily illustrates a top perspective view of the bite frame 200. FIG. 2B exemplarily illustrates a top plan view of the bite frame 200. The bite frame 200 comprises a handle 101 and an arcuate frame element 102 rigidly connected to an upper end 101a of the handle 101 and defining a generally narrow hollow arcuate opening 103 as disclosed in the detailed description of FIGS. 1A-1D. The handle 101 further comprises an opening 101b, for example, of a circular shape for engaging with an indicating fork 1101b of a panoramic front guide 1101 exemplarily illustrated in FIG. 11, during a panoramic X-ray imaging process. In this embodiment, the bite frame 200 further comprises radio-opaque markers 201 positioned at predetermined locations along an inner rim 102a of the arcuate frame element 102. The radio-opaque markers 201 are configured as metal balls and are used in panoramic X-ray imaging to provide clear, accurate reference points to positions of the upper jaw and the lower jaw in two-dimensional (2D) panoramic X-ray images of the upper jaw and lower jaw, a 3D panoramic X-ray image created using the 2D panoramic X-ray images of the upper jaw and the lower jaw, and 3D scanned images of a bite impression for the determination of the 3D relation between the upper jaw and the lower jaw as disclosed in the detailed description of FIGS. 12A-12D, FIGS. 13A-13B, and FIGS. 14A-14B. The radio-opaque markers 201 are visible under an X-ray fluoroscope or a panoramic X-ray machine and are typically made from a high density metal, for example, aluminum, lead, iron, stainless steel, platinum, gold, tantalum, etc.

Figure 3:
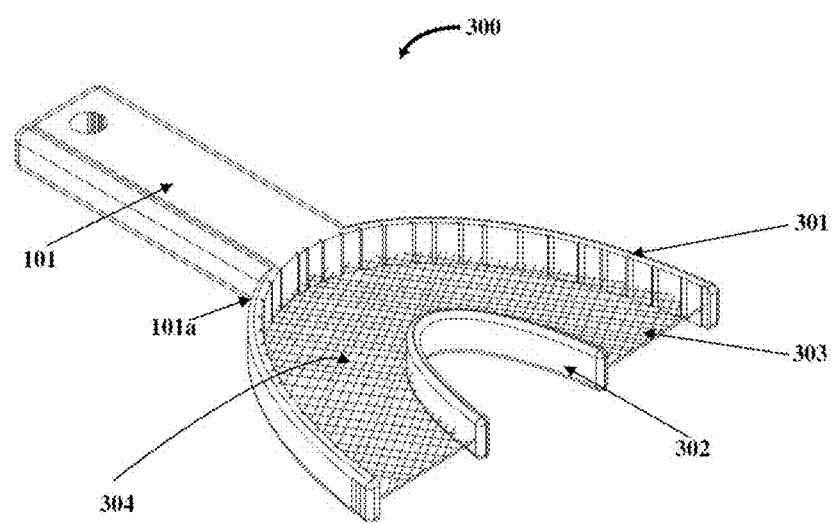
FIG. 3 exemplarily illustrates a top perspective view of an embodiment of the bite frame for enabling determination of a three-dimensional relation between an upper jaw and a lower jaw of a patient with natural dentition.

FIG. 3 exemplarily illustrates a top perspective view of an embodiment of the bite frame 100 exemplarily illustrated in FIGS. 1A-1D, for enabling determination of a three-dimensional (3D) relation between an upper jaw and a lower jaw of a patient with natural dentition. The bite frame 300 for a patient with natural dentition comprises a handle 101, an outer arcuate frame element 301, an inner arcuate frame element 302, and a mesh element 303. The outer arcuate frame element 301 is rigidly connected to an upper end 101a of the handle 101. The inner arcuate frame element 302 is positioned at a predetermined distance from the outer arcuate frame element 301. The inner arcuate frame element 302 and the outer arcuate frame element 301 are configured to define a generally wide arcuate opening 304 therebetween for mounting the mesh element 303. For a patient with natural dentition, a closed bite frame 300 with a wide arcuate or arch opening 304 filled with the mesh element 303 is used. The mesh element 303 is configured to receive a bite registration material for registering a bite impression comprising an impression of the upper jaw and an impression of the lower jaw, and thereafter enabling the determination of the 3D relation between the upper jaw and the lower jaw. The bite frame 300 is constructed to register impressions of the upper jaw and the lower jaw. The impressions on the bite registration material contain the 3D relation between the upper jaw and the lower jaw. For an edentulous patient, an open bite frame 100 exemplarily illustrated in FIG. 1A and FIG. 1D, or 200 exemplarily illustrated in FIGS. 2A-2B, with a narrow arcuate or arch opening 103 without the mesh element 303 is used. For the edentulous patient, the mesh element 303 is replaced by the bite shaped member 500, 700, or 900 exemplarily illustrated in FIGS. 5A-5D, FIGS. 7A-7E, and FIGS. 9A-9H respectively, inserted into the narrow hollow arcuate opening 103 of the arcuate frame element 102 of the bite frame 100 or 200.

Figure 4:
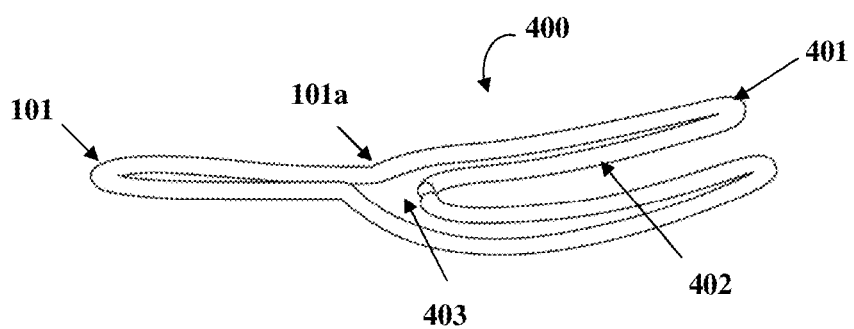
FIG. 4 exemplarily illustrates a side perspective view of another embodiment of the bite frame for enabling determination of a three-dimensional relation between an upper jaw and a lower jaw of an edentulous patient.

FIG. 4 exemplarily illustrates a side perspective view of another embodiment of the bite frame 100 exemplarily illustrated in FIGS. 1A-1D for enabling determination of a three-dimensional (3D) relation between an upper jaw and a lower jaw of an edentulous patient. The bite frame 400 exemplarily illustrated in FIG. 4 comprises a handle 101 and an arcuate frame element 401 extending continuously from an upper end 101a of the handle 101 and defining a narrow hollow arcuate opening 403. The bite frame 400 exemplarily illustrated in FIG. 4 is a continuous wire type bite frame. In this embodiment, the bite frame 400 is configured to form an occlusion curve 402, for example, a Curve of Spee, as exemplarily illustrated in FIG. 4. The Curve of Spee is an anatomic curvature of an occlusal alignment of teeth, beginning at the tip of the lower canine, following the buccal cusps of the natural premolars and molars and continuing to the anterior border of the ramus.

FIGS. 5A-5D exemplarily illustrate different views of an arcuate bite shaped member 500. The bite shaped member 500, 700, or 900 exemplarily illustrated in FIGS. 5A-5D, FIGS. 7A-7E, and FIGS. 9A-9H is configured to be inserted into and accommodated within the narrow hollow arcuate opening 103 of the bite frame 100 exemplarily illustrated in FIG. 1A-1D, or 200 exemplarily illustrated in FIGS. 2A-2B. The bite shaped member 500, 700, or 900 comprises a body structure 501, 701, or 901, an upper channel 502, 702, or 902 of a configurable shape, and a lower channel 504, 703, or 903 of a configurable shape. The body structure 501, 701, or 901 is configured in one of multiple flexible geometric shapes in different embodiments of the bite shaped member 500, 700, or 900. The flexible geometric shapes comprise, for example, a generally arcuate shape, a generally cylindrical shape, a generally tubular shape, a generally trefoil shape, a generally polygonal shape, a generally cuboidal shape, a generally polyform shape, a generally quatrefoil shape, etc. The bite shaped member 500 with an arcuate body structure 501, referred to herein as an "arcuate bite shaped member", is exemplarily illustrated FIGS. 5A-5D. The bite shaped member 700 with a block shaped body structure 701, referred to herein as a "block type bite shaped member", is exemplarily illustrated in FIGS. 7A-7E. The bite shaped member 900 with an elongate body structure 901, referred to herein as an "elongate bite shaped member", is exemplarily illustrated in FIG. 9A, FIG. 9C, FIG. 9E, and FIG. 9G.

In an embodiment, partial features of the bite shaped member 700, for example, the upper channel 702 and/or the lower channel 703, and one or more partial portions of the bite shaped member 700 can be used to form a flexible bite shaped member 700 as exemplarily illustrated in FIGS. 7A-7E. These partial features are configurable for creating different flexible bite shaped members, for example, 700, 900, etc. The partial portion is configured to register a portion of the upper jaw and the lower jaw, for example, for creating a partial removable prosthesis, restoring a dental crown, or restoring a dental bridge. For example, the partial portion is used when only one half or a portion of the upper jaw and the lower jaw is required to be registered. The configurable shape of the upper channel 502, 702, or 902 and the lower channel 504, 703, or 903 of the bite shaped member 500, 700, or 900 is, for example, one of a generally V shape, a generally rectangular shape, a generally arcuate shape, a generally cuboidal shape, a generally hemispherical shape, a generally elliptical shape, a generally trapezoidal shape, a generally cylindrical shape, a generally tubular shape, or any combination thereof.

Figure 5A:
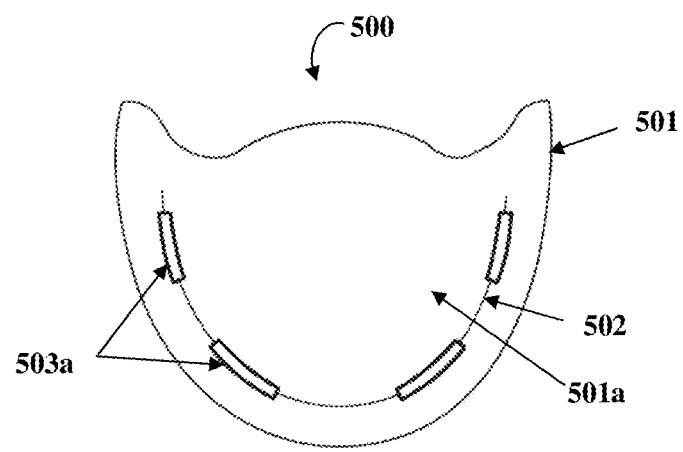
FIG. 5A exemplarily illustrates a top plan view of an arcuate bite shaped member, showing an upper channel and upper windows positioned at configurable locations along the upper channel.
Figure 5B:
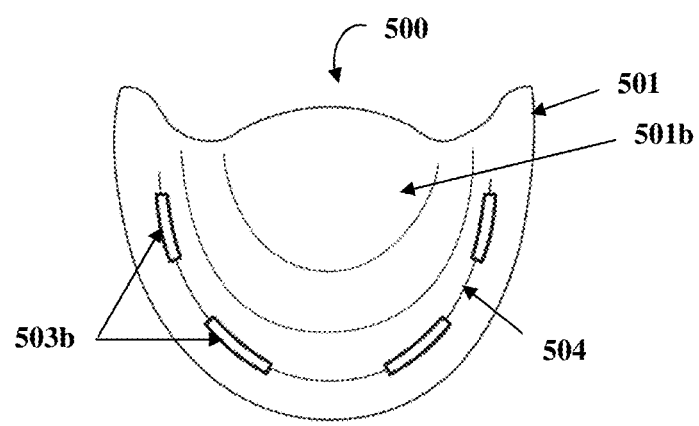
FIG. 5B exemplarily illustrates a bottom view of the arcuate bite shaped member, showing a lower channel and lower windows positioned at configurable locations along the lower channel.

In the embodiment exemplarily illustrated in FIGS. 5A-5D, the arcuate bite shaped member 500 comprises an arcuate body structure 501, an upper channel 502 exemplarily illustrated in FIG. 5A, a lower channel 504 exemplarily illustrated in FIG. 5B, and windows 503a and 503b exemplarily illustrated in FIGS. 5A-5B. The arcuate body structure 501 has an upper surface 501a exemplarily illustrated in FIG. 5A, and a lower surface 501b exemplarily illustrated in FIG. 5B, separated by a mid-section 501c exemplarily illustrated in FIGS. 5C-5D. The upper surface 501a of the arcuate body structure 501 is configured to conform to the upper jaw of a patient. The lower surface 501b of the arcuate body structure 501 is configured to conform to the lower jaw of the patient. The upper channel 502 is of a configurable shape, for example, a generally arcuate shape, and is defined on the upper surface 501a of the arcuate body structure 501. FIG. 5A exemplarily illustrates a top plan view of the arcuate bite shaped member 500, showing the upper channel 502 and upper windows 503a positioned at configurable locations along the upper channel 502. The upper channel 502 is configured to receive a bite registration material and engage an upper ridge of the upper jaw to register an impression of the upper ridge of the upper jaw. The lower channel 504 is of a configurable shape, for example, a generally arcuate shape, and is defined on a lower surface 501b of the arcuate body structure 501. FIG. 5B exemplarily illustrates a bottom view of the arcuate bite shaped member 500, showing the lower channel 504 and lower windows 503b positioned at configurable locations along the lower channel 504. The lower channel 504 is configured to receive the bite registration material and engage a lower ridge of the lower jaw to register an impression of the lower ridge of the lower jaw. The registration of the impression of the upper ridge of the upper jaw and the impression of the lower ridge of the lower jaw that constitute a bite impression enables determination of the three-dimensional (3D) relation between the upper jaw and the lower jaw.

The upper windows 503a and the lower windows 503b of the bite shaped member 500 are, for example, rectangular shaped windows. The upper windows 503a are positioned along the upper channel 502 on the upper surface 501a of the arcuate body structure 501. The lower windows 503b are positioned along the lower channel 504 on the lower surface 501b of the arcuate body structure 501. The upper windows 503a and the lower windows 503b are separated by a space 501e therebetween, within the bite shaped member 500. The space 501e is configured to receive the bite registration material from the upper channel 502 and the lower channel 504 through the upper windows 503a and the lower windows 503b respectively. The upper windows 503a, in fluid communication with the lower windows 503b, allow flow of the received bite registration material from the upper channel 502 to the lower channel 504 to register a vertical distance between the upper ridge of the upper jaw and the lower ridge of the lower jaw for the determination of the three-dimensional (3D) relation between the upper jaw and the lower jaw.

When the bite frame 100 exemplarily illustrated in FIG. 1A-1D, or 200 exemplarily illustrated in FIG. 2A-2B, or 400 exemplarily illustrated in FIG. 4, with the accommodated arcuate bite shaped member 500 is inserted into a patient's mouth, the upper windows 503a exemplarily illustrated in FIG. 5A, connect to the upper ridge of the upper jaw, while the lower windows 503b exemplarily illustrated in FIG. 5B, connect to the lower ridge of the lower jaw of the patient's mouth. Along the channels 502 and 504, the windows 503a and 503b that connect to the upper ridge and the lower ridge of the edentulous patient respectively, are opened to allow flow of the bite registration material through the windows 503a and 503b into the space 501e extending between the upper channel 502 and the lower channel 504 to register the vertical distance between the upper ridge of the upper jaw and the lower ridge of the lower jaw. In an embodiment, arcuate bite shaped members 500 of different thicknesses can be used for different vertical distances between the upper jaw and the lower jaw among patients.

Figure 5C:
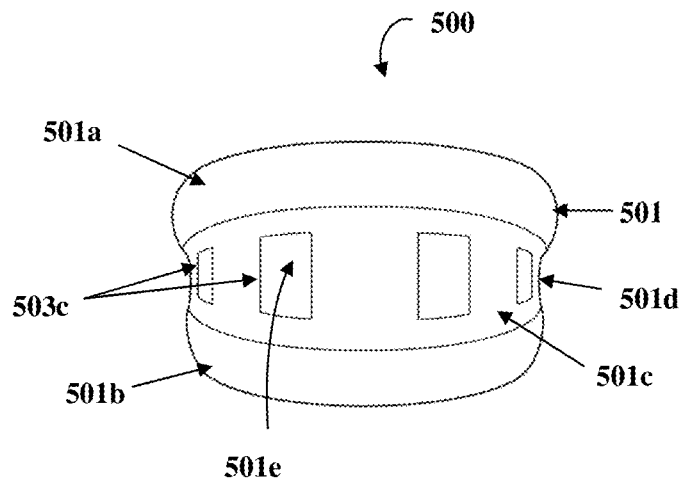
FIG. 5C exemplarily illustrates a front elevation view of the arcuate bite shaped member, showing supplementary windows positioned at configurable locations along a mid-section of an arcuate body structure of the arcuate bite shaped member.
Figure 5D:
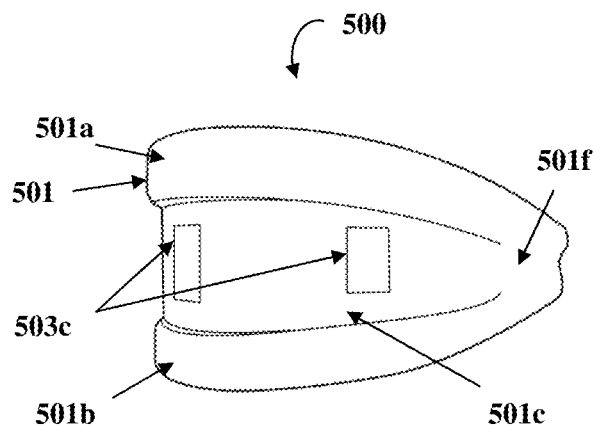
FIG. 5D exemplarily illustrates a side elevation view of the arcuate bite shaped member.

FIG. 5C and FIG. 5D exemplarily illustrate a front elevation view and a side elevation view respectively, of the arcuate bite shaped member 500. Thinning 501d along the midline or the mid-section 501c of the arcuate bite shaped member 500 exemplarily illustrated in FIG. 5C, enables the arcuate bite shaped member 500 to fit into the bite frame 100 exemplarily illustrated in FIG. 1A-1D, or 200 exemplarily illustrated in FIG. 2A-2B, or 400 exemplarily illustrated in FIG. 4. The vertical dimensions towards the posterior 501f of the arcuate body structure 501 of the arcuate bite shaped member 500 exemplarily illustrated in FIG. 5D, are tapered to mimic the narrow posterior vertical dimensions between the upper jaw and the lower jaw. In an embodiment as exemplarily illustrated in FIG. 5C-5D, the arcuate bite shaped member 500 further comprises supplementary windows 503c positioned at configurable locations, for example, equally spaced locations along the mid-section 501c of the arcuate body structure 501 of the arcuate bite shaped member 500. The supplementary windows 503c are in fluid communication with the space 501e exemplarily illustrated in FIG. 5C, between the upper channel 502 and the lower channel 504 of the arcuate bite shaped member 500. The supplementary windows 503c are, for example, rectangular shaped windows configured to allow excess bite registration material to flow out from the space 501e between the upper channel 502 and the lower channel 504. The locations of the windows 503a, 503b, and 503c exemplarily illustrated in FIGS. 5A-5D, can be configured during fabrication of the arcuate bite shaped member 500.

Figure 6A:
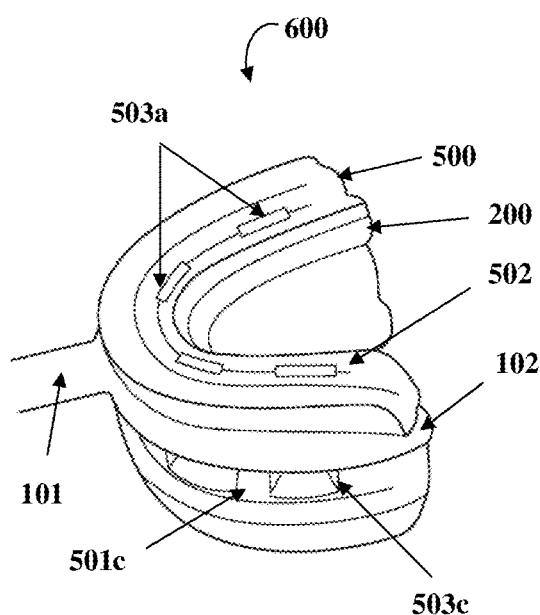
FIG. 6A exemplarily illustrates a side perspective view of a bite registration apparatus comprising the bite frame and the arcuate bite shaped member.

FIG. 6A exemplarily illustrates a side perspective view of a bite registration apparatus 600 comprising the bite frame, for example, 200 and the arcuate bite shaped member 500. The arcuate frame element 102 of the bite frame 200 defines a generally narrow hollow arcuate opening 103 exemplarily illustrated in FIGS. 2A-2B, to accommodate the arcuate bite shaped member 500. The arcuate bite shaped member 500 is compressed and inserted into the generally narrow hollow arcuate opening 103 of the bite frame 200. The mid-section 501c of the arcuate bite shaped member 500 can be configured as a thin layer and slid into the narrow hollow arcuate opening 103 defined by the arcuate frame element 102 of the bite frame 200. The arcuate bite shaped member 500 is configured to slide along the arcuate frame element 102 of the bite frame 200 until the arch of the bite frame 200 fits into the arch shaped mid-section 501c of the arcuate bite shaped member 500 as exemplarily illustrated in FIG. 6A. A flexible arcuate bite shaped member 500 made using a foam material inserted into the bite frame 200 is exemplarily illustrated in FIG. 6A.

Figure 6B:
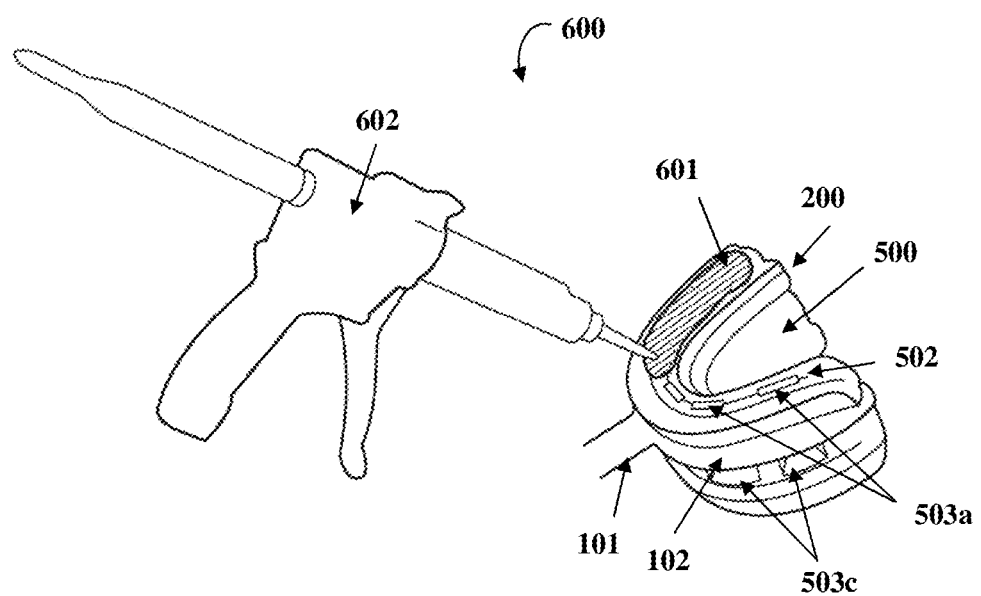
FIGS. 6B-6C exemplarily illustrate application and flow of a bite registration material into the arcuate bite shaped member accommodated in the bite frame of the bite registration apparatus.
Figure 6C:
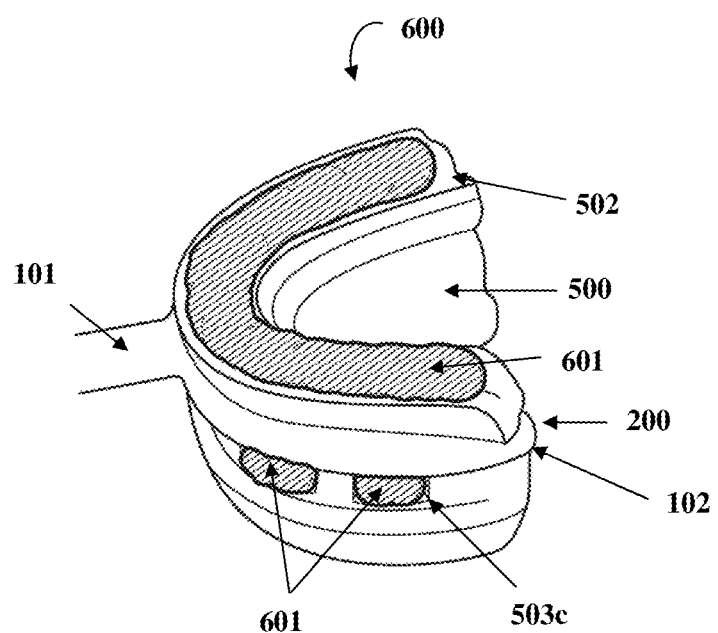

FIGS. 6B-6C exemplarily illustrate application and flow of a bite registration material 601 into the arcuate bite shaped member 500 accommodated in the bite frame 200 of the bite registration apparatus 600. An example of the bite registration material 601 is the Blu-Mousse® thixotropic vinyl polysiloxane material of Parkell Products, Inc., that provides an extended setting time to load additional bite registration material 601 and time guide a patient's proper jaw position. After a dental practitioner or a clinician injects the bite registration material 601 using an injection tool 602 exemplarily illustrated in FIG. 6B, into the upper channel 502, the lower channel 504, and the windows 503a of the arcuate bite shaped member 500, the bite frame 200 is inserted into the patient's mouth, and the patient is instructed to bite into the arcuate bite shaped member 500. The bite registration material 601 flows into the windows 503a from the upper channel 502 of the arcuate bite shaped member 500 as exemplarily illustrated in FIG. 6B, to the lower channel 504 of the arcuate bite shaped member 500. Excess bite registration material 601 flows out from the supplementary windows 503c of the arcuate bite shaped member 500 as exemplarily illustrated in FIG. 6C.

Figure 6D:
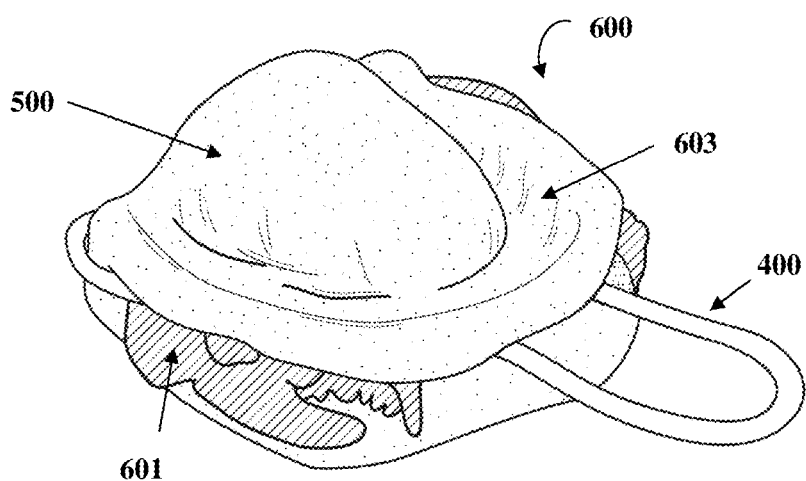
FIG. 6D exemplarily illustrates an impression of an upper ridge of an upper jaw registered on the bite registration material applied into the arcuate bite shaped member accommodated within the bite frame of the bite registration apparatus.

FIG. 6D exemplarily illustrates an impression 603 of an upper ridge of an upper jaw registered on the bite registration material 601 applied into the arcuate bite shaped member 500 accommodated within the bite frame 400 exemplarily illustrated in FIG. 4. When the patient bites into the arcuate bite shaped member 500, an impression 603 of the upper ridge of the upper jaw as exemplarily illustrated in FIG. 6D, and the lower ridge of the lower jaw of the patient is registered on the bite registration material 601. The registration of a bite impression comprising the impression 603 of the upper ridge of the upper jaw and the impression of the lower ridge of the lower jaw enables determination of the three-dimensional (3D) relation between the upper jaw and the lower jaw. The bite impression contains the three-dimensional (3D) relation between the upper and lower ridges of an edentulous patient.

FIGS. 7A-7E exemplarily illustrate different views of an embodiment of the bite shaped member, herein referred to as "a block type bite shaped member" and referenced by the numeral 700. The block type bite shaped member 700 is configured to be inserted into and accommodated within the narrow hollow arcuate opening 103 of the arcuate frame element 102 of the bite frame 100 exemplarily illustrated in FIG. 1A-1D, or 200 exemplarily illustrated in FIG. 2A-2B. The block type bite shaped member 700 is formed of a soft, flexible porous material, for example, a reticulated foam configurable for changing its shape and form for folding and accommodating the block type bite shaped member 700 into the narrow hollow arcuate opening 103 of the arcuate frame element 102 of the bite frame 100 or 200. The flexible porous material is configured to absorb the bite registration material 601 exemplarily illustrated in FIGS. 6B-6D. In an embodiment, the block type bite shaped member 700 is formed of a flexible porous material with a generally low pore per inch (PPI) value to allow enhanced penetration of the bite registration material 601 into an upper channel 702 and a lower channel 703 of the block type bite shaped member 700 for registration of the impressions of the upper ridge of the upper jaw and the lower ridge of the lower jaw. As used herein, "pore per inch" indicates cell count of the flexible porous material, that is, the number of cells in the flexible porous material per running inch of the flexible porous material. The type of foam used to create the block type bite shaped member 700 can be characterized by density, hardness, tensile strength, and the PPI value of the foam. Therefore, the foam used is a soft, biologically safe foam with a low PPI value. A low PPI value, for example, 40 indicates large pores in the foam which allow additional bite registration material 601 to penetrate into the foam and form a more rigid impression of the upper ridge of the upper jaw and the lower ridge of the lower jaw of the patient.

Figure 7A:
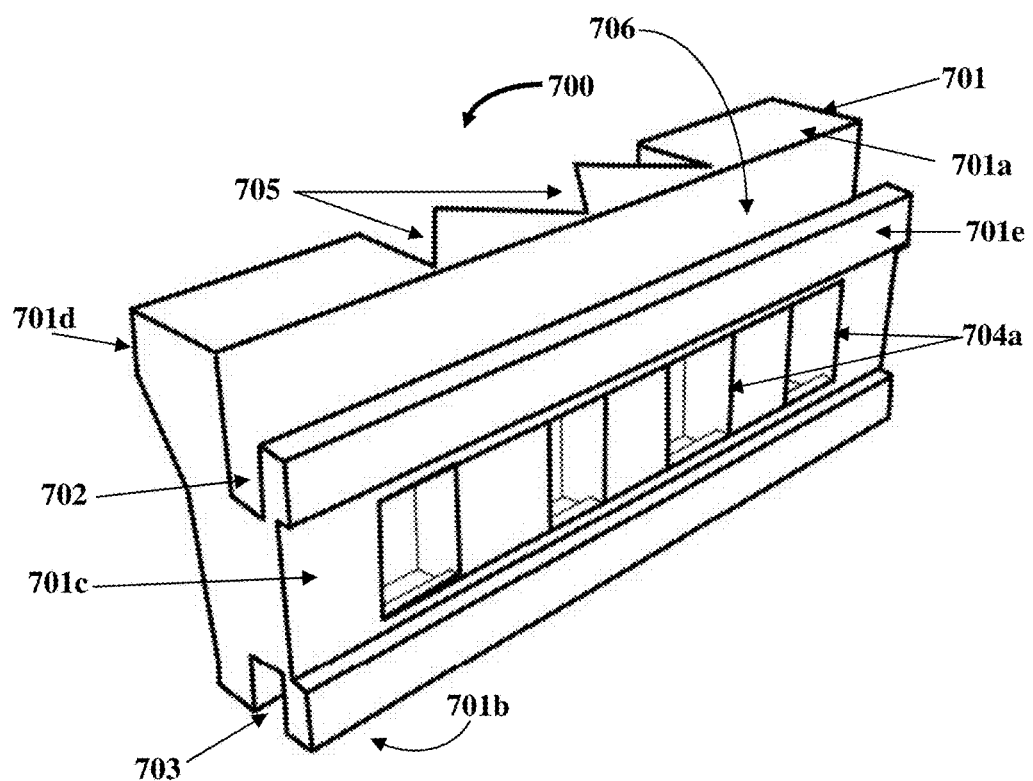
FIG. 7A exemplarily illustrates a perspective view of an embodiment of the bite shaped member, showing a block type body structure, an upper channel, a lower channel, and supplementary windows.
Figure 7B:
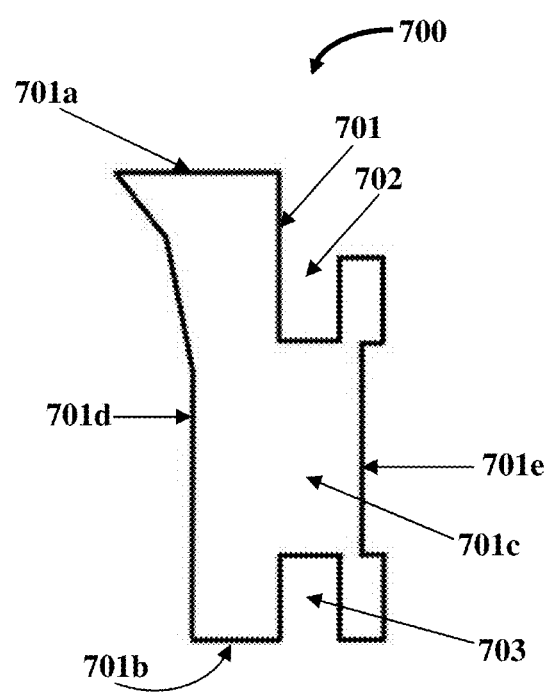
FIG. 7B exemplarily illustrates a front elevation view of the embodiment of the bite shaped member shown in FIG. 7A, showing the upper channel and the lower channel of the bite shaped member.
Figure 7C:
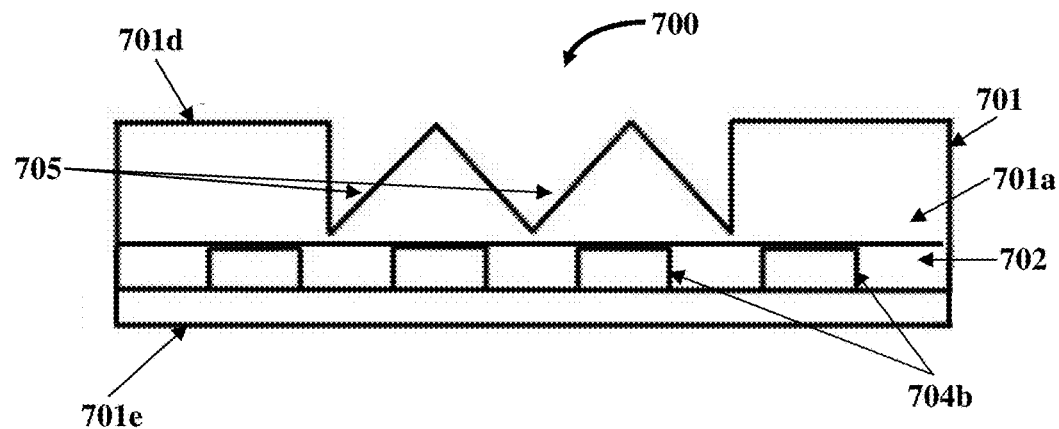
FIG. 7C exemplarily illustrates a top plan view of the embodiment of the bite shaped member shown in FIG. 7A, showing an upper section of the block type body structure and upper windows positioned along the upper channel on the upper section of the body structure.
Figure 7D:
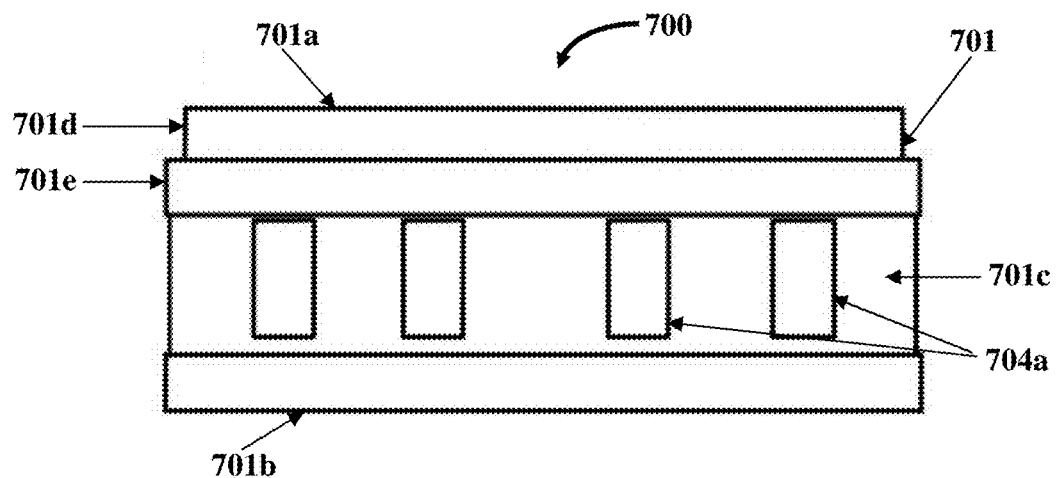
FIG. 7D exemplarily illustrates a right side elevation view of the embodiment of the bite shaped member shown in FIG. 7A, showing the supplementary windows on a mid-section of the block type body structure.

The block type bite shaped member 700 comprises a body structure 701, an upper channel 702 exemplarily illustrated in FIGS. 7A-7C, a lower channel 703 exemplarily illustrated in FIGS. 7A-7B, and windows 704a and 704b exemplarily illustrated in FIG. 7A and FIGS. 7C-7D. In this embodiment, the body structure 701 is of a multi-geometric shape. FIG. 7A exemplarily illustrates a perspective view of the block type bite shaped member 700, showing the block type body structure 701, the upper channel 702, the lower channel 703, and the supplementary windows 704a. The body structure 701 has an upper section 701a configured to conform to the upper jaw of the patient, and a lower section 701b configured to conform to the lower jaw of the patient. The upper section 701a and the lower section 701b of the body structure 701 are separated by a mid-section 701c. The upper channel 702 is, for example, of a rectangular shape and is defined on the upper section 701a of the body structure 701. The upper channel 702 is configured to receive a bite registration material 601 and engage an upper ridge of the upper jaw to register an impression of the upper ridge of the upper jaw. The lower channel 703 is, for example, of a rectangular shape and is defined on the lower section 701b of the body structure 701. The lower channel 703 is configured to receive the bite registration material 601 and engage a lower ridge of the lower jaw to register an impression of the lower ridge of the lower jaw. FIG. 7B exemplarily illustrates a front elevation view of the block type bite shaped member 700, showing the upper channel 702 and the lower channel 703 of the block type bite shaped member 700. The registration of the impression of the upper ridge of the upper jaw and the impression of the lower ridge of the lower jaw that constitute a bite impression enables the determination of the three-dimensional (3D) relation between the upper jaw and the lower jaw.

The block type bite shaped member 700 comprises upper windows 704b as exemplarily illustrated in FIG. 7C, and lower windows (not shown). The upper windows 704b and the lower windows of the block type bite shaped member 700 are, for example, rectangular shaped windows. The upper windows 704b are positioned along the upper channel 702 on the upper section 701a of the body structure 701. FIG. 7C exemplarily illustrates a top plan view of the block type bite shaped member 700, showing the upper section 701a of the block type body structure 701 and the upper windows 704b positioned along the upper channel 702 on the upper section 701a of the block type body structure 701. The lower windows are positioned along the lower channel 703 on the lower section 701b of the body structure 701. The upper windows 704b and the lower windows are separated by a space 706 therebetween, within the block type bite shaped member 700. The space 706 is configured to receive the bite registration material 601 from the upper channel 702 and the lower channel 703 through the upper windows 704b and the lower windows respectively. The upper windows 704b, in fluid communication with the lower windows, allow flow of the received bite registration material 601 from the upper channel 702 to the lower channel 703 as exemplarily illustrated in FIG. 8D, to register a vertical distance between the upper ridge of the upper jaw and the lower ridge of the lower jaw for the determination of the three-dimensional (3D) relation between the upper jaw and the lower jaw.

Figure 7E:
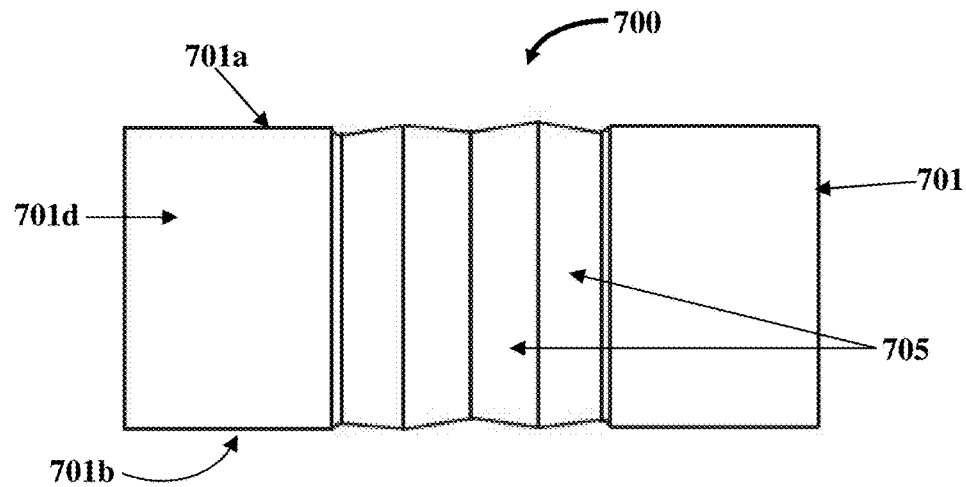
FIG. 7E exemplarily illustrates a left side elevation view of the embodiment of the bite shaped member shown in FIG. 7A, showing grooves positioned along an opposing side wall of the block type body structure.

In an embodiment, supplementary windows 704a are positioned at configurable locations along the mid-section 701c of the body structure 701 on an opposing side wall 701e of the body structure 701 with openings into the upper channel 702 and the lower channel 703 of the body structure 701 as exemplarily illustrated in FIG. 7A and FIG. 7D. FIG. 7D exemplarily illustrates a right side elevation view of the block type bite shaped member 700, showing the supplementary windows 704a on the mid-section 701c of the block type body structure 701. The supplementary windows 704a are in fluid communication with the space 706 between the upper channel 702 and the lower channel 703 of the block type bite shaped member 700 to allow the excess bite registration material 601 to flow out from the space 706. The upper channel 702 and the lower channel 703 extend into the mid-section 701c of the body structure 701 and open out into the supplementary windows 704a. The impression material or the bite registration material 601 from the upper windows 704b and the lower windows penetrates through the space 706 extending from the upper channel 702 to the lower channel 703 within the block type bite shaped member 700 and extrudes out from the side supplementary windows 704a. In an embodiment, the block type bite shaped member 700 further comprises multiple grooves 705, for example, of a generally V shape as exemplarily illustrated in FIG. 7A, FIG. 7C, and FIG. 7E, positioned at configurable locations on an opposing side wall 701d of the body structure 701. FIG. 7E exemplarily illustrates a left side elevation view of the block type bite shaped member 700, showing the grooves 705 positioned along the opposing side wall 701d of the block type body structure 701. The V-shaped grooves 705 are configured to facilitate folding and accommodation of the block type bite shaped member 700 into the narrow hollow arcuate opening 103 of the arcuate frame element 102 of the bite frame 100 exemplarily illustrated in FIG. 1A-1D, or 200 exemplarily illustrated in FIGS. 2A-2B.

Figure 8A:
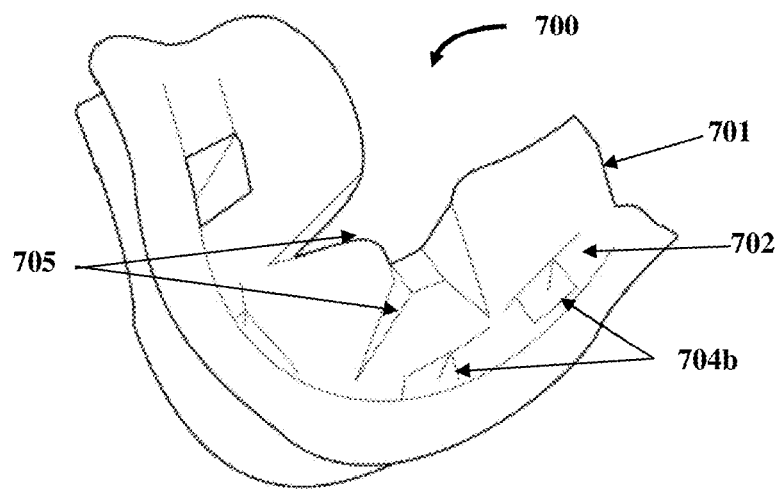
FIG. 8A exemplarily illustrates a top perspective view of a flexible bite shaped member formed of a foam material.
Figure 8B:
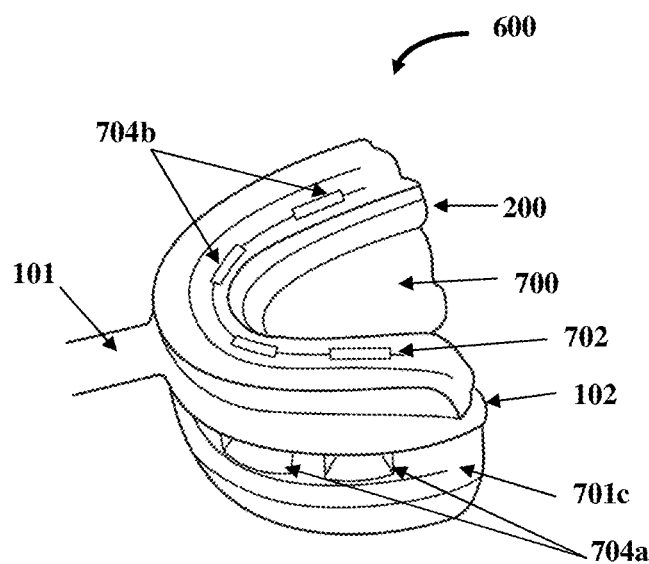
FIG. 8B exemplarily illustrates a side perspective view of the bite registration apparatus, showing the bite frame accommodating the flexible bite shaped member shown in FIG. 8A.
Figure 8C:
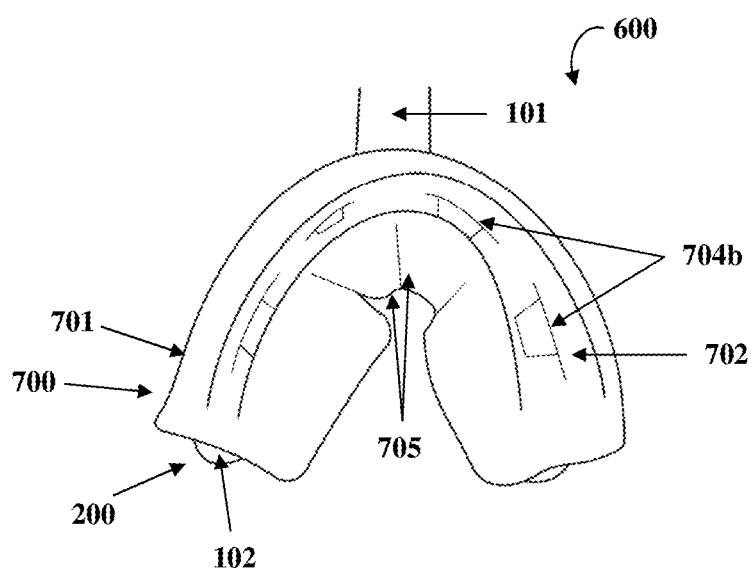
FIG. 8C exemplarily illustrates a top perspective view of the bite registration apparatus, showing the bite frame accommodating the flexible bite shaped member shown in FIG. 8A.
Figure 8D:
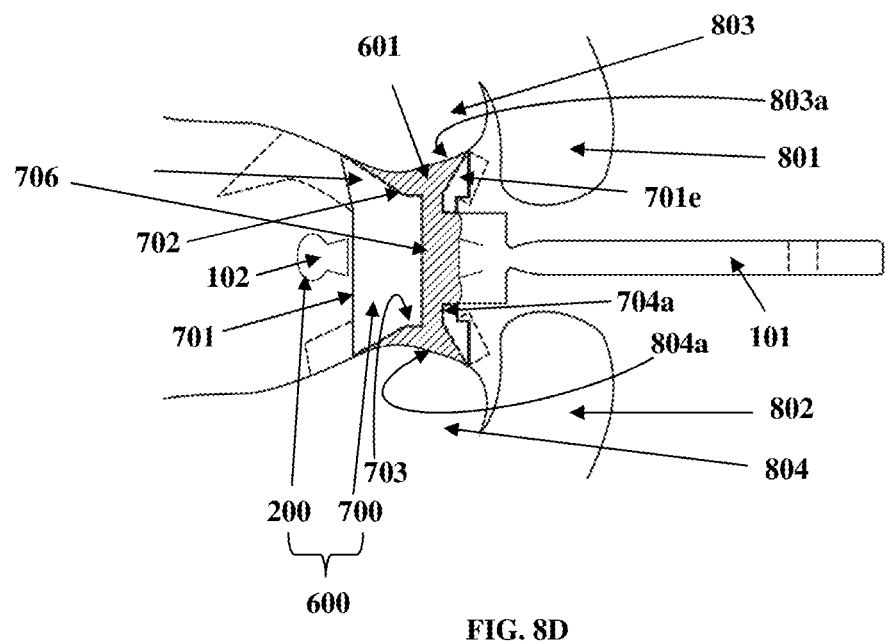
FIG. 8D exemplarily illustrates the bite registration apparatus inserted into the mouth of an edentulous patient.
Figure 9A:
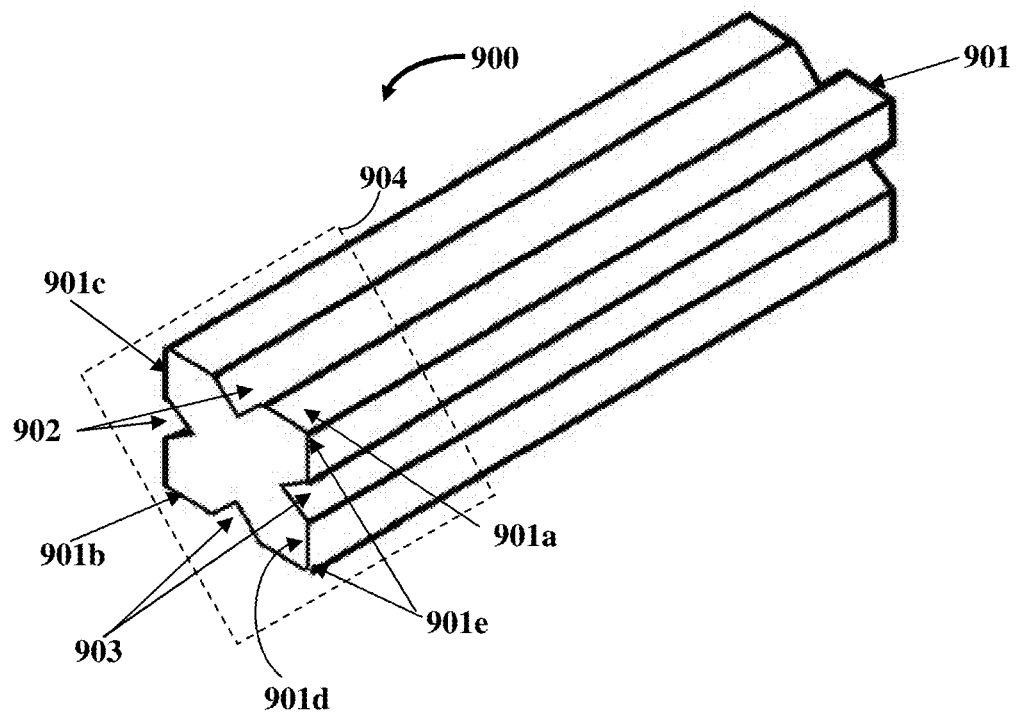
FIGS. 9A-9H exemplarily illustrate different views of another embodiment of the bite shaped member comprising an elongate body structure with V-shaped channels.
Figure 9B:
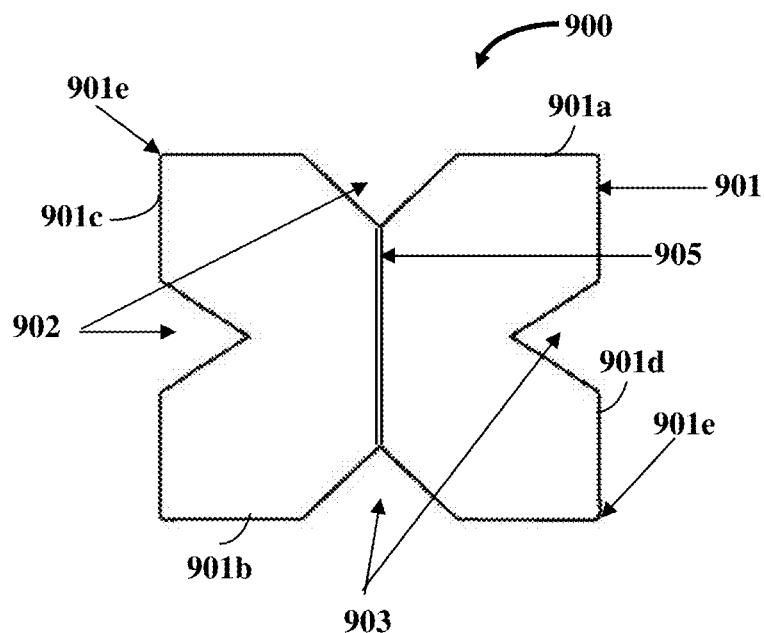
Figure 9C:
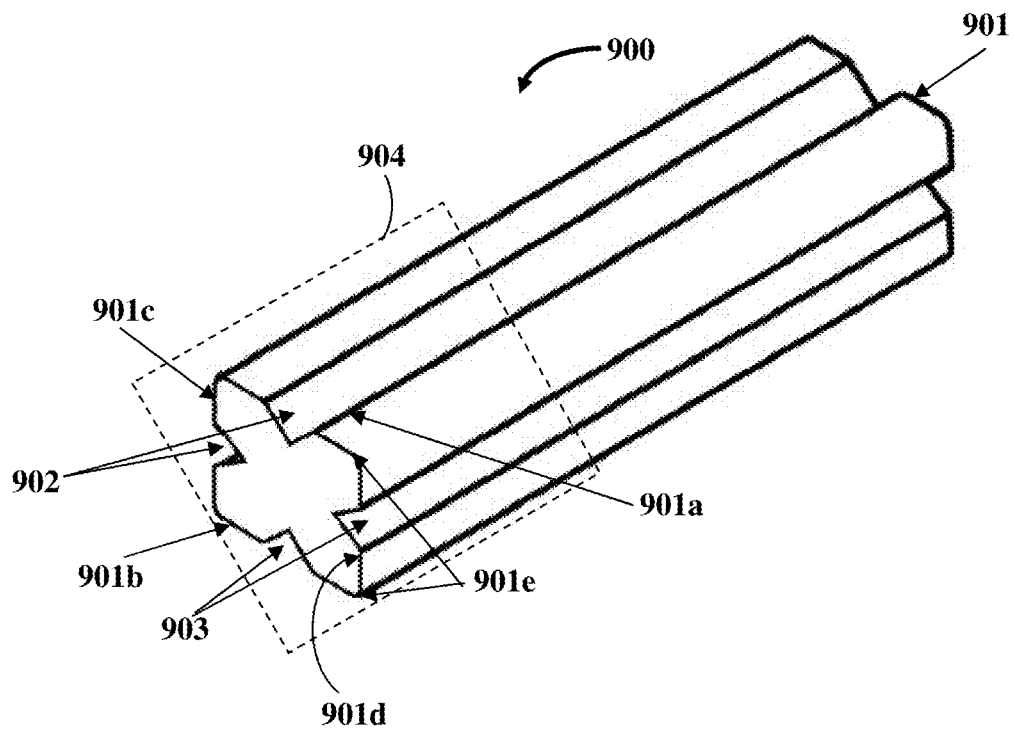
Figure 9D:
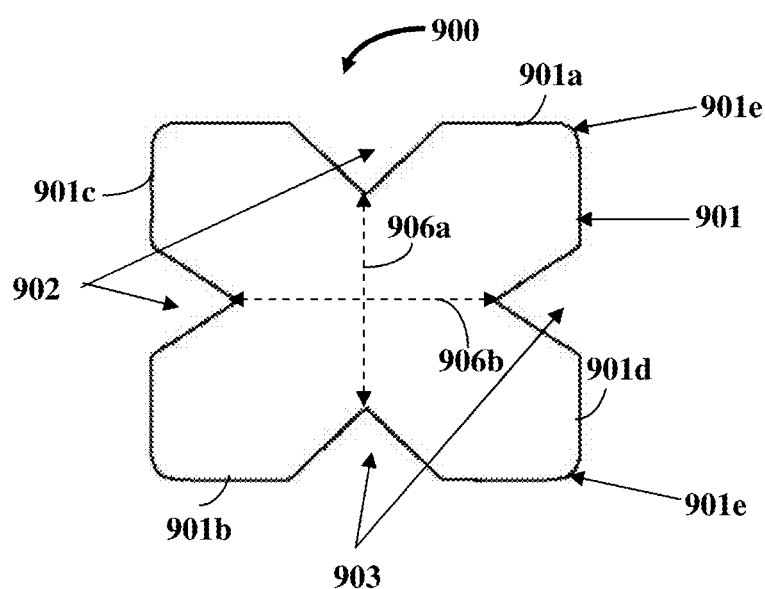
Figure 9E:
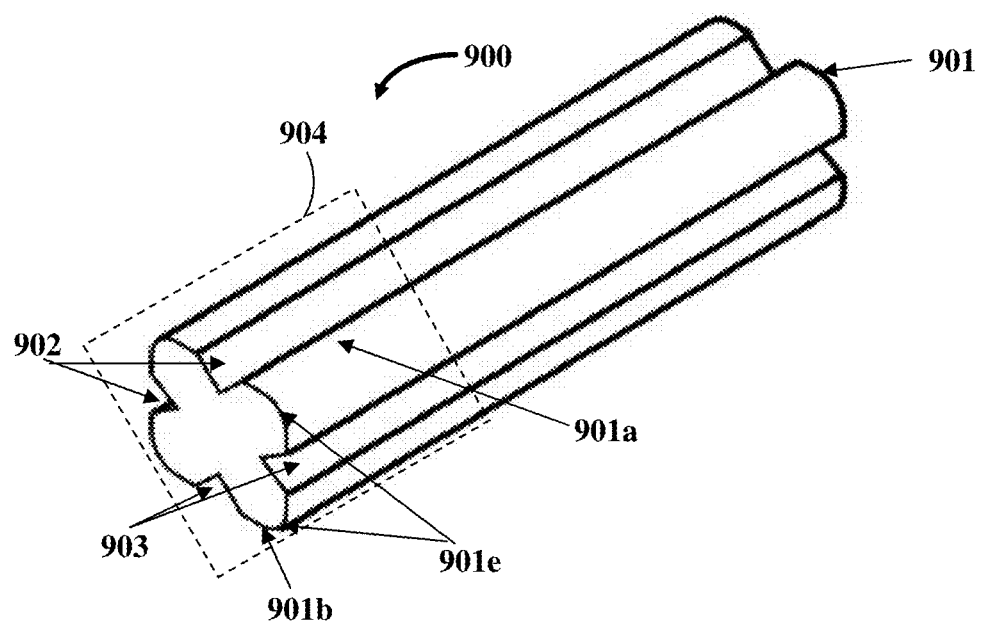
Figure 9F:
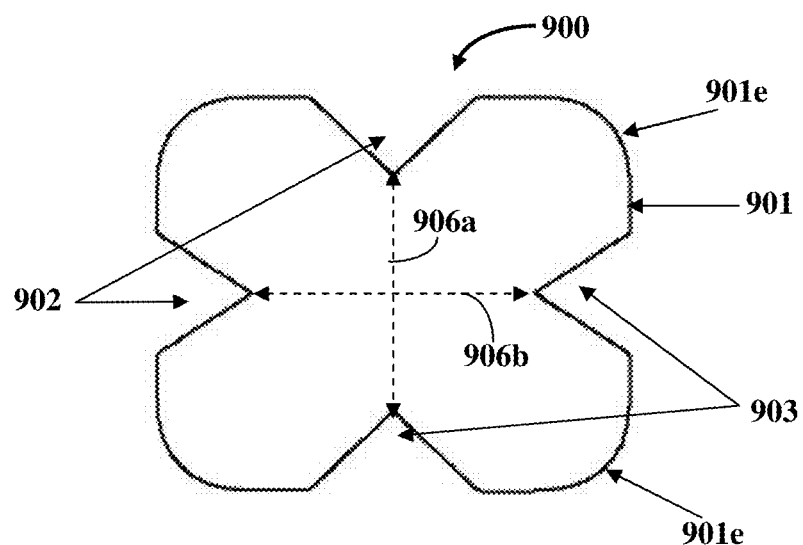
Figure 9G:
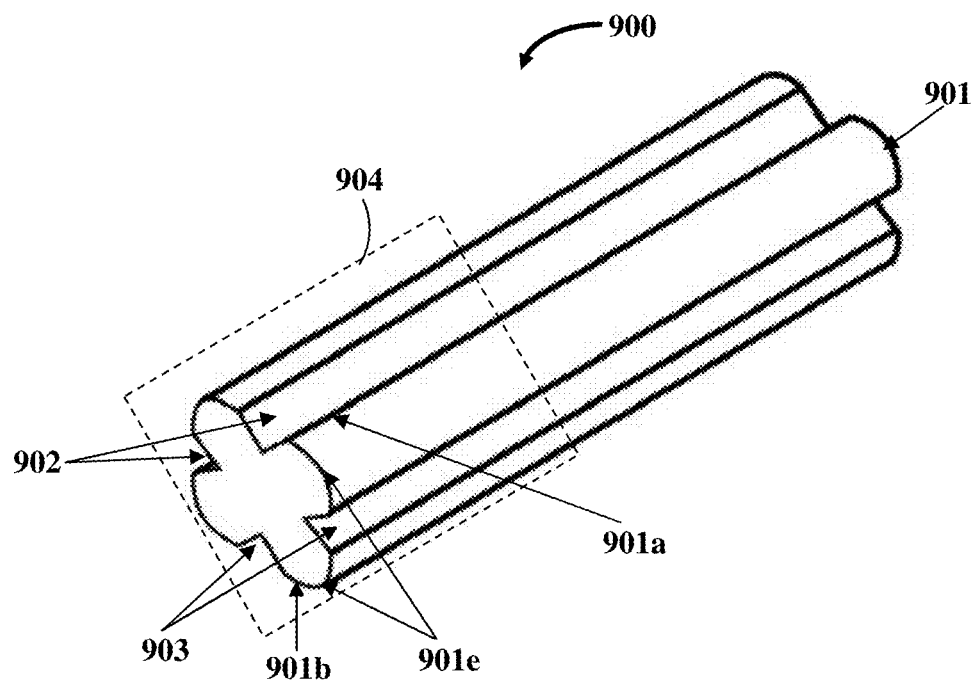
Figure 9H:
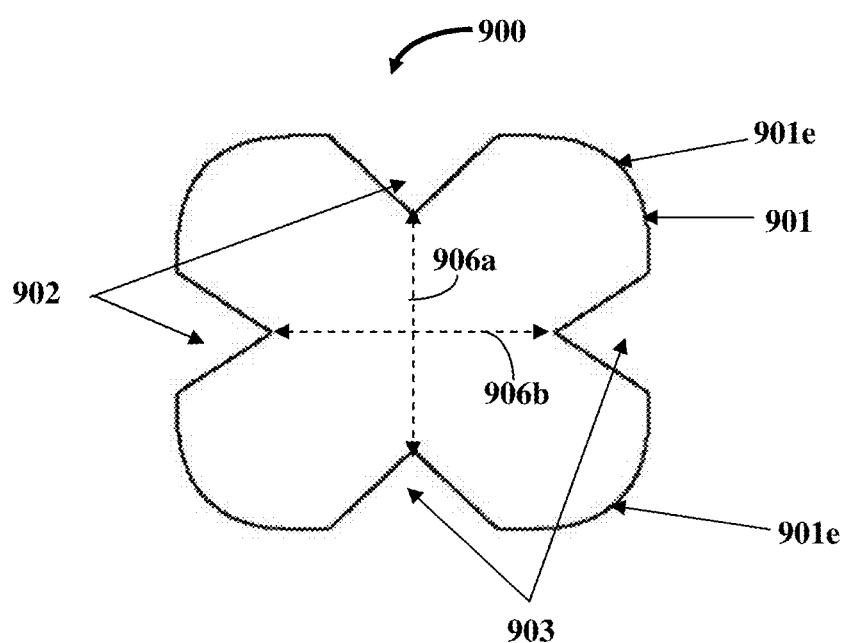

FIG. 8A exemplarily illustrates a top perspective view of a flexible bite shaped member 700 formed of a foam material. FIGS. 8B-8C exemplarily illustrate different views of the bite registration apparatus 600, showing the bite frame 200 accommodating the flexible bite shaped member 700 shown in FIG. 8A. FIG. 8B exemplarily illustrates a side perspective view of the bite registration apparatus 600, showing the bite frame 200 accommodating the flexible bite shaped member 700 of FIG. 8A. FIG. 8C exemplarily illustrates a top perspective view of the bite registration apparatus 600, showing the bite frame 200 accommodating the flexible bite shaped member 700 of FIG. 8A. FIG. 8D exemplarily illustrates the bite registration apparatus 600 inserted into the mouth of an edentulous patient.

The flexible porous material of the flexible block type bite shaped member 700 is bent as exemplarily illustrated in FIG. 8A, and inserted into the narrow hollow arcuate opening 103 exemplarily illustrated in FIGS. 2A-2B, defined by the arcuate frame element 102 of the bite frame 200 as exemplarily illustrated in FIGS. 8B-8C. After a dental practitioner or a clinician injects a bite registration material 601 into the upper channel 702, the lower channel 703, the upper windows 704b, and the lower windows (not shown) of the inserted flexible block type bite shaped member 700, the bite registration apparatus 600 is inserted into an edentulous patient's mouth between the upper lip 801 and the lower lip 802 as exemplarily illustrated in FIG. 8D. The upper windows 704b of the flexible block type bite shaped member 700 connect to the upper ridge 803a of the upper jaw 803, while the lower windows connect to the lower ridge 804a of the lower jaw 804 of the edentulous patient's mouth.

The bite registration material 601 flows from the upper channel 702 and the lower channel 703 into the upper windows 704b and the lower windows of the flexible block type bite shaped member 700. Along the channels 702 and 703, the upper windows 704b and the lower windows that connect to the upper ridge 803a and the lower ridge 804a of the edentulous patient respectively, are opened to allow flow of the bite registration material 601 into the space 706 extending between the upper channel 702, the lower channel 703 to register the vertical distance between the upper ridge 803a and the lower ridge 804a. The patient is instructed to bite into the flexible block type bite shaped member 700 until the flexible block type bite shaped member 700 reaches an optimal vertical distance required by the dental practitioner or the clinician for registering the bite impression. The flexible block type bite shaped member 700 changes shape when the patient bites into the flexible block type bite shaped member 700 as indicated by dashed lines in FIG. 8D. The opposing side walls 701d and 701e of the body structure 701 of the flexible block type bite shaped member 700 extend outwardly when the patient bites into the flexible block type bite shaped member 700. Impressions of the upper ridge 803a of the upper jaw 803 and the lower ridge 804a of the lower jaw 804 of the edentulous patient are registered on the bite registration material 601 injected into the upper channel 702 and the lower channel 703 of the flexible block type bite shaped member 700 respectively, which enables determination of the desired upper and lower jaw relation. The bite impression contains the three-dimensional (3D) relation between the upper ridge 803a of the upper jaw 803 and the lower ridge 804a of the lower jaw 804.

FIGS. 9A-9H exemplarily illustrate different views of another embodiment of the bite shaped member 900 comprising an elongate body structure 901 with V-shaped channels 902 and 903. FIG. 9A, FIG. 9C, FIG. 9E, and FIG. 9G exemplarily illustrate perspective views of the bite shaped member 900 configured to be accommodated within the bite frame 100 exemplarily illustrated in FIG. 1A-1D, or 200 exemplarily illustrated in FIG. 2A-2B, or 400 exemplarily illustrated in FIG. 4, for enabling determination of a three-dimensional (3D) relation between an upper jaw 803 and a lower jaw 804 exemplarily illustrated in FIG. 8D. The bite shaped member 900 comprises an elongate body structure 901 and V-shaped channels 902 and 903. The elongate body structure 901 has opposing surfaces 901a, 901b and 901c, 901d as exemplarily illustrated in FIG. 9A. The V-shaped channels 902 and 903 are configured on the opposing surfaces, for example, 901a, 901b and 901c, 901d of the elongate body structure 901. The V-shaped channels 902 and 903 are separated by different distances 906a and 906b from each other as exemplarily illustrated in FIG. 9D, FIG. 9F, and FIG. 9H. For example, one set of opposing V-shaped channels 902 and 903 configured on the opposing surfaces 901a and 901b are separated by a short distance 906a, while another set of opposing V-shaped channels 902 and 903 configured on the opposing surfaces 901c and 901d are separated by a longer distance 906b as exemplarily illustrated in FIG. 9D. The V-shaped channels 902 and 903 are configured to interchangeably engage the upper ridge 803a of the upper jaw 803 and the lower ridge 804a of the lower jaw 804 exemplarily illustrated in FIG. 10C.

The V-shaped channels 902 and 903 are also configured to receive a bite registration material 601 exemplarily illustrated in FIGS. 6B-6D, for registering a bite impression comprising an impression of the upper ridge 803a of the upper jaw 803 and an impression of the lower ridge 804a of the lower jaw 804, and thereafter enabling determination of the three-dimensional relation between the upper jaw 803 and the lower jaw 804. In this embodiment, the bite shaped member 900 is further configured to be interchangeably positioned in different directions to enable vertical distance adjustments of the bite shaped member 900 for the registration of the bite impression comprising the impressions of the upper jaw 803 and the lower jaw 804. For example, if the vertical distance between the upper jaw 803 and the lower jaw 804 of a patient is small, the bite shaped member 900 can be turned by 90 degrees to allow a shorter vertical dimension, and the V-shaped channels 902 and 903 will perform their respective functions of receiving the bite registration material 601 for registering the bite impression. Positioning the bite shaped member 900 in different directions exposes any set of opposing V-shaped channels 902 and 903 to the upper ridge 803a of the upper jaw 803 and the lower ridge 804a of the lower jaw 804. The position of the bite shaped member 900 is changed based on an estimate of the vertical distance between the upper jaw 803 and the lower jaw 804. The V-shaped channels 902 and 903 can be used in different directions, which offer a different vertical distance 906a or 906b in the bite shaped member 900.

If a patient is a partially edentulous patient, that is, a patient with partially missing teeth, certain portions 904 of the bite shaped member 900 as exemplarily illustrated in FIG. 9A, FIG. 9C, FIG. 9E, and FIG. 9G, can be cut out and used to obtain an impression of the missing teeth area. A partial portion 904 is used when an impression of only a half or a portion of the upper jaw 803 and the lower jaw 804 is required to be registered for creation of a partial removable prosthesis, or for a dental crown restoration, or a dental bridge restoration. For the dental crown restoration and the dental bridge restoration, a partial portion 904 of the bite shaped member 900 can also be used to register a section of a restoration area.

FIG. 9B, FIG. 9D, FIG. 9F, and FIG. 9H exemplarily illustrate front elevation views of the embodiment of the bite shaped member 900 shown in FIG. 9A, FIG. 9C, FIG. 9E, and FIG. 9G respectively. The elongate body structure 901 of the bite shaped member 900 comprises opposing distal end portions 901e configured in multiple shapes to conform to oral cavities of different sizes. The differently shaped distal end portions 901e are designed for oral cavities of different sizes. If the patient has natural dentition, a deeper V-shaped channel 902 or 903 is configured to allow a closer biting distance between the upper teeth and the lower teeth. In an embodiment, the bite shaped member 900 further comprises an opening 905 extending from the upper V-shaped channel 902 to the lower V-shaped channel 903 as exemplarily illustrated in FIG. 9B, for allowing a closer biting distance between the upper teeth and the lower teeth. The elongate body structure 901 is also configured in multiple shapes to conform to oral cavities of different sizes.

Figure 10A:
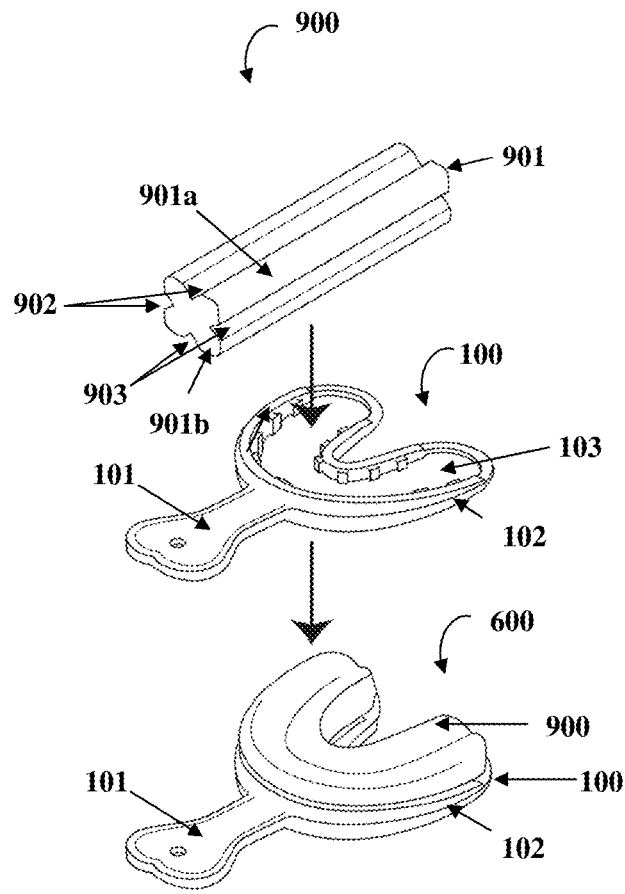
FIG. 10A exemplarily illustrates engagement of the embodiment of the bite shaped member shown in FIGS. 9A-9H, into a bite frame of the bite registration apparatus.
Figure 10B:
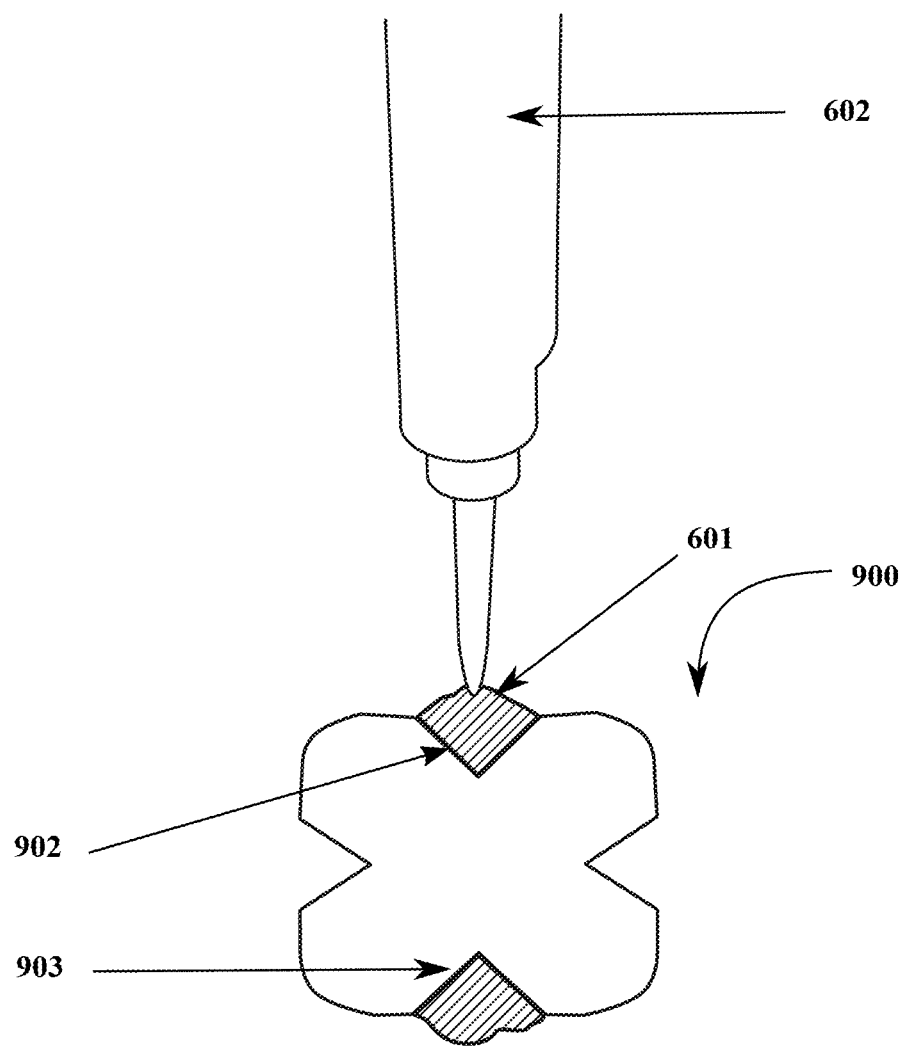
FIG. 10B exemplarily illustrates application of a bite registration material into the V-shaped channels of the embodiment of the bite shaped member shown in FIGS. 9A-9H.
Figure 10C:
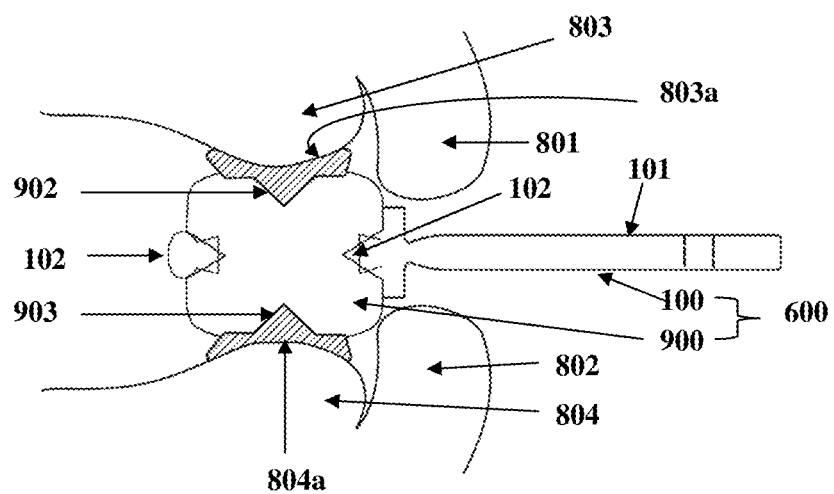
FIG. 10C exemplarily illustrates the bite registration apparatus comprising the bite frame with the embodiment of the bite shaped member shown in FIGS. 9A-9H, inserted into the mouth of an edentulous patient.

FIG. 10A exemplarily illustrates engagement of the embodiment of the bite shaped member 900 shown in FIGS. 9A-9H, into the bite frame 100 of the bite registration apparatus 600. The bite shaped member 900 is folded and inserted into the bite frame 100 as exemplarily illustrated in FIG. 10A, which is then inserted into the mouth of an edentulous patient. FIG. 10B exemplarily illustrates application of a bite registration material 601 into the V-shaped channels 902 and 903 of the bite shaped member 900. The bite registration material 601 is injected into the V-shaped channels 902 and 903 of the bite shaped member 900 using an injection tool 602. FIG. 10C exemplarily illustrates the bite registration apparatus 600 comprising the bite frame 100 with the bite shaped member 900 inserted into the mouth of the edentulous patient. The bite shaped member 900 is inserted into the bite frame 100, which is then inserted into the edentulous patient's mouth between the upper lip 801 and the lower lip 802 of the edentulous patient as exemplarily illustrated in FIG. 10C. The patient is instructed to bite into the bite shaped member 900. When the patient bites into the bite registration material 601 applied in the V-shaped channels 902 and 903 of the bite shaped member 900, impressions of the upper ridge 803a of the upper jaw 803 and the lower ridge 804a of the lower jaw 804 of the edentulous patient constituting the bite impression are created in the bite registration material 601, thereby enabling determination of the desired upper and lower jaw relation. The bite impression contains the three-dimensional (3D) relation between the upper ridge 803a of the upper jaw 803 and the lower ridge 804a of the lower jaw 804 of the edentulous patient.

Figure 11:
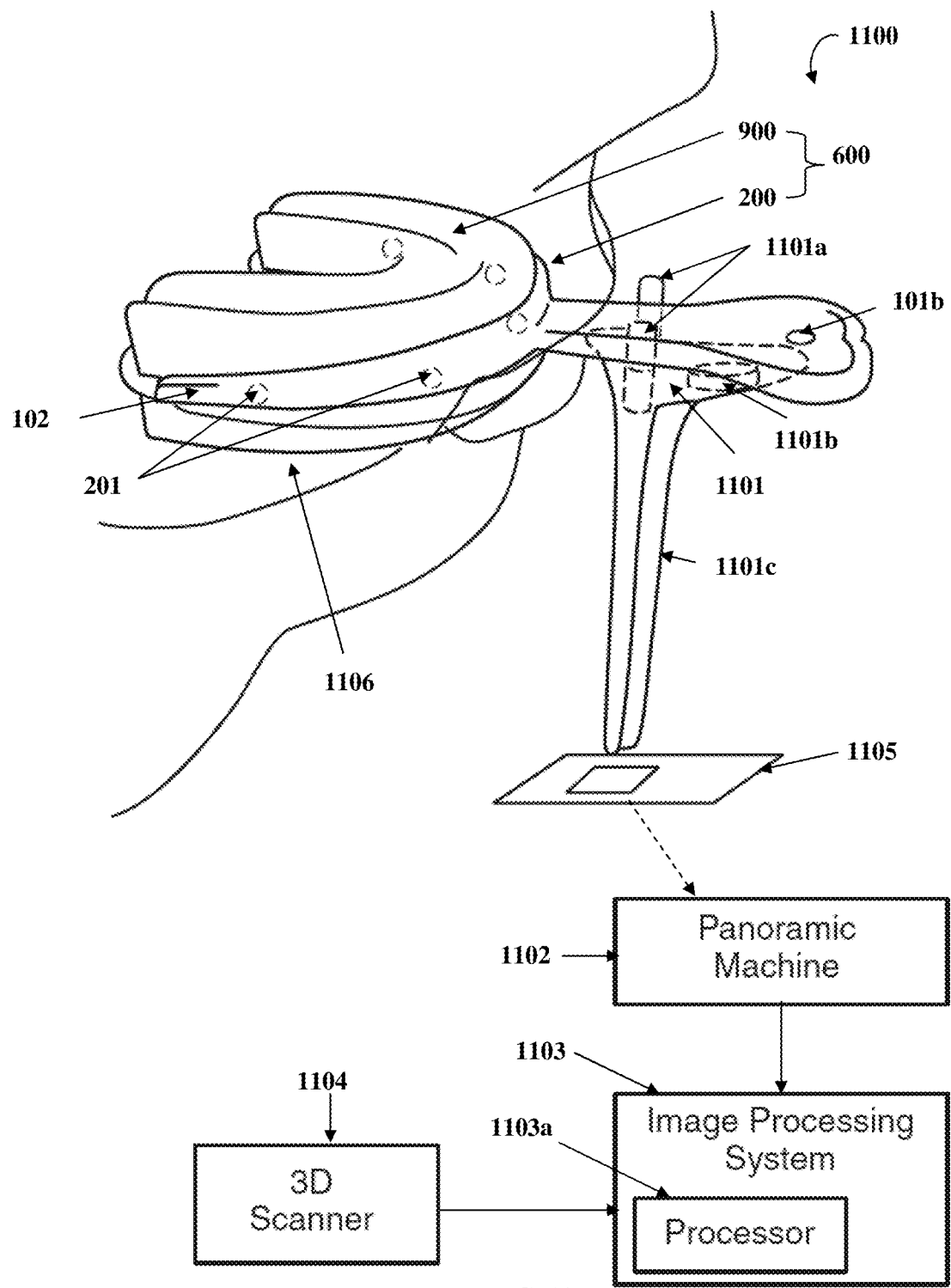
FIG. 11 exemplarily illustrates a system for determining a three-dimensional relation between an upper jaw and a lower jaw with reference to temporomandibular joints of a patient.

FIG. 11 exemplarily illustrates a system 1100 for determining a three-dimensional (3D) relation between an upper jaw 803 and a lower jaw 804 exemplarily illustrated in FIG. 8D, with reference to temporomandibular joints (TMJ) of a patient. The system 1100 disclosed herein comprises the bite registration apparatus 600, a panoramic front guide 1101, a panoramic machine 1102, a 3D image scanning and processing system referred to herein as an "image processing system" 1103, and a 3D scanner 1104. The bite registration apparatus 600 comprises the bite frame 200 and the bite shaped member, for example, 900. The bite frame 200 comprises the handle 101, the arcuate frame element 102, and the radio-opaque markers 201 as disclosed in the detailed description of FIGS. 2A-2B. The panoramic front guide 1101 comprises holding forks 1101a, an indicating fork 1101b, and a holding frame 1101c. The panoramic front guide 1101 engages with the handle 101 of the bite frame 200. The handle 101 of the bite frame 200 can be slid between the holding forks 1101a of the panoramic front guide 1101. The indicating fork 1101b on the panoramic front guide 1101 can be slid into a circular opening 101b on the handle 101 of the bite frame 200. The holding frame 1101c helps to locate the bite frame 200 in a panoramic imaging process. The bite frame 200 follows an outer surface of a cheek area 1106 along a bite line. The bite shaped member, for example, 900 comprises the body structure 901, the upper channel 902, and the lower channel 903 as disclosed in the detailed description of FIGS. 9A-9H.

The radio-opaque markers 201 are positioned at configurable intervals along the arch of the bite frame 200. The panoramic front guide 1101 is operably connected to the panoramic machine 1102. The panoramic front guide 1101 engages with a guide slot 1105 on the panoramic machine 1102. The guide slot 1105 guides a patient's head position 1102 during the panoramic imaging process. The panoramic machine 1102 captures two-dimensional (2D) panoramic X-ray images of the upper jaw 803 and the lower jaw 804 with the bite frame 200 in and around the patient's mouth and creates a three-dimensional (3D) panoramic X-ray image. The panoramic machine 1102 is operably coupled to the image processing system 1103. The image processing system 1103 comprises a processor 1103a configured to process images captured and created by the panoramic machine 1102 and the three-dimensional (3D) scanner 1104.

The 3D scanner 1104, for example, a structured white light scanner provides 3D scanned images of the bite impression registered on the bite registration material 601 exemplarily illustrated in FIGS. 6B-6D. The metal marking reference points provided by the radio-opaque markers 201 of the bite frame 200 are recorded in the panoramic X-ray images and can be used for determining the 3D geometric relation of the upper jaw 803 and the lower jaw 804 with reference to the temporomandibular joints. The image processing system 1103 matches the 3D panoramic X-ray image with the 3D scanned images by matching the metal marking reference points on the 3D panoramic X-ray image of the upper jaw 803 and the lower jaw 804 with the reference points on the 3D scanned images of the bite impression.

Figure 12A:
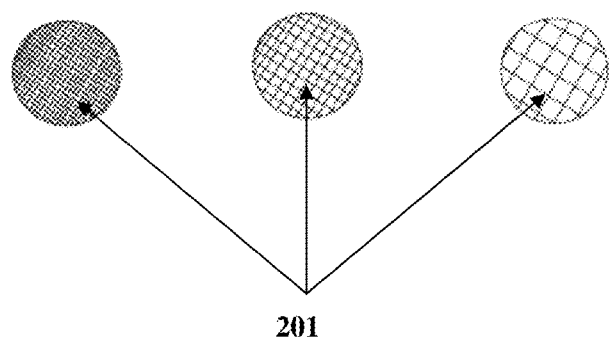
FIGS. 12A-12D exemplarily illustrate radio-opaque markers used for determining a three-dimensional relation between an upper jaw and a lower jaw with reference to temporomandibular joints of a patient.
Figure 12B:
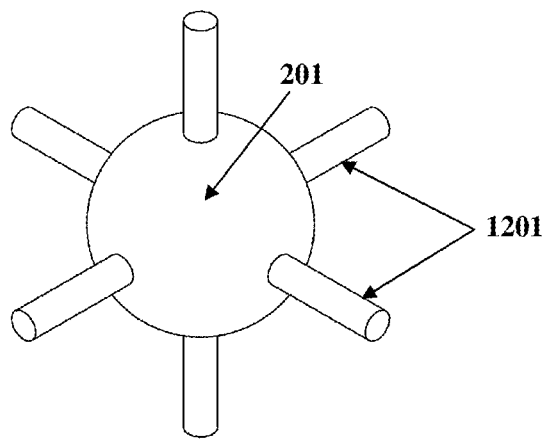
Figure 12C:
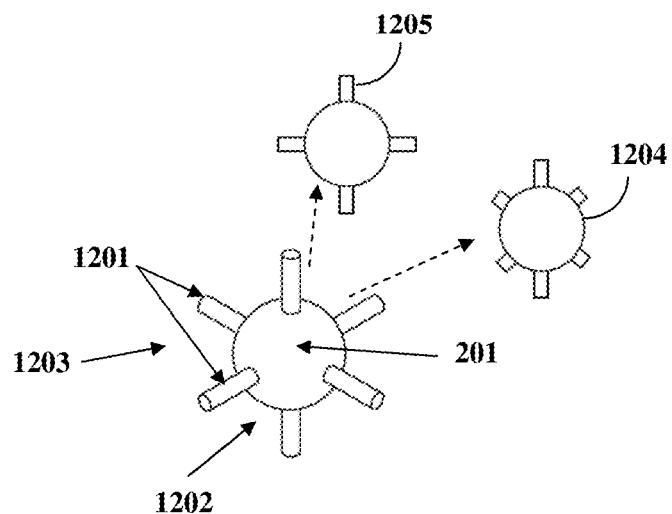
Figure 12D:
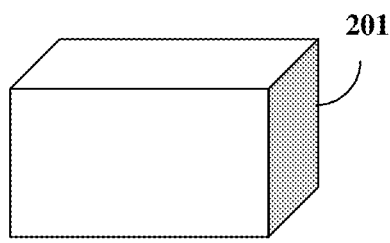

FIGS. 12A-12D exemplarily illustrate radio-opaque markers 201 used for determining a three-dimensional (3D) relation between an upper jaw 803 and a lower jaw 804 exemplarily illustrated in FIG. 8D, with reference to temporomandibular joints of a patient. The radio-opaque markers 201 are configured with different densities as exemplarily illustrated in FIG. 12A, to distinguish the radio-opaque markers 201 from other radio-opaque structures. The radio-opaque markers 201 exemplarily illustrated in FIGS. 12A-12C are configured as metal balls. In an embodiment, orientation bars 1201 are positioned on each of the radio-opaque markers 201 as exemplarily illustrated in FIGS. 12B-12C. The orientation bars 1201 extend outwardly from each of the radio-opaque markers 201. The orientation bars 1201 facilitate calculation of a 3D orientation of each radio-opaque marker 201 in a projected image, for example, 1204 or 1205 of each radio-opaque marker 201. The projected images 1204 and 1205 are recorded in the 2D and 3D panoramic X-ray images. Typically, when X-rays encounter a radio-opaque marker 201 in two different directions, for example, 1202 and 1203 as exemplarily illustrated in FIG. 12C, two different projected images 1205 and 1204 of the radio-opaque marker 201 are obtained. In the direction 1202, only two of the orientation bars 1201 of the radio-opaque marker 201 are seen in the projected image 1205. In the direction 1203, three orientation bars 1201 of the radio-opaque marker 201 are seen in the projected image 1204. However, the orientation bars 1201 in the projected image 1204 are aligned at different angles when compared to the original angles of the orientation bars 1201 on the radio-opaque marker 201. The angle of orientation of the orientation bars 1201 reflects the orientation of the radio-opaque marker 201, and the orientation of the orientation bar 1201 with respect to the direction of the X-ray can be mathematically calculated. In an embodiment, the radio-opaque marker 201 is configured as a rectangular cuboid as exemplarily illustrated in FIG. 12D, or as a rectangular cube. The cuboidal radio-opaque marker 201 can be used to indicate the orientation of the radio-opaque marker 201. A shadow cast by each radio-opaque marker 201 in different directions or at different angles reflects the orientation of the radio-opaque marker 201.

Figure 13A:
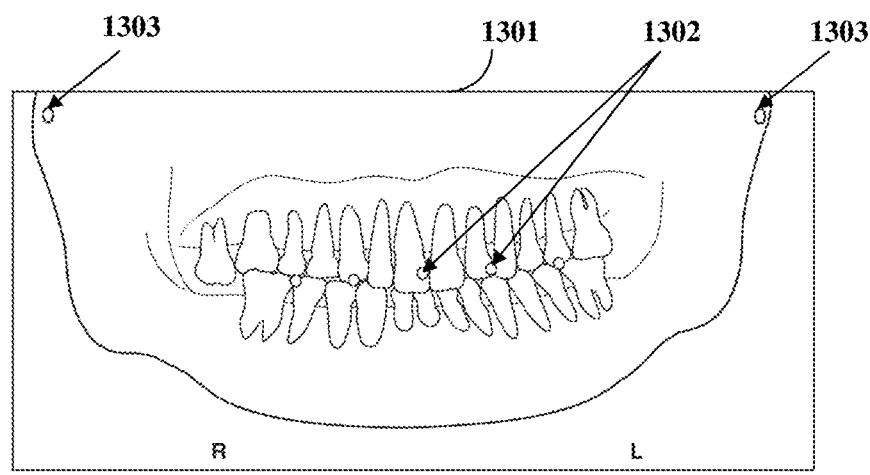
FIG. 13A exemplarily illustrates a two-dimensional panoramic X-ray image of a mouth of a patient with an inserted bite frame, showing reference points provided by the radio-opaque markers.

FIG. 13A exemplarily illustrates a two-dimensional (2D) panoramic X-ray image 1301 of a patient's mouth with an inserted bite frame 200, showing reference points 1302 and 1303 provided by the radio-opaque markers 201 exemplarily illustrated in FIGS. 2A-2B, and external radio-opaque markers (not shown). The 2D panoramic X-ray images 1301 are captured using the panoramic machine 1102 exemplarily illustrated in FIG. 11, when the bite frame 200 is inserted into the patient's mouth. The 2D panoramic X-ray images 1301 contain positions of the upper jaw 803 and the lower jaw 804 exemplarily illustrated in FIG. 8D, respectively. The reference points 1302 provided by the radio-opaque markers 201 in the bite frame 200 are recorded while capturing the 2D panoramic X-ray images 1301. In an embodiment, external radio-opaque markers (not shown) are placed below the ears near the temporomandibular joint (TMJ) area. The reference points 1303 provided by these external radio-opaque markers are also recorded in the 2D panoramic X-ray images 1301.

Figure 13B:
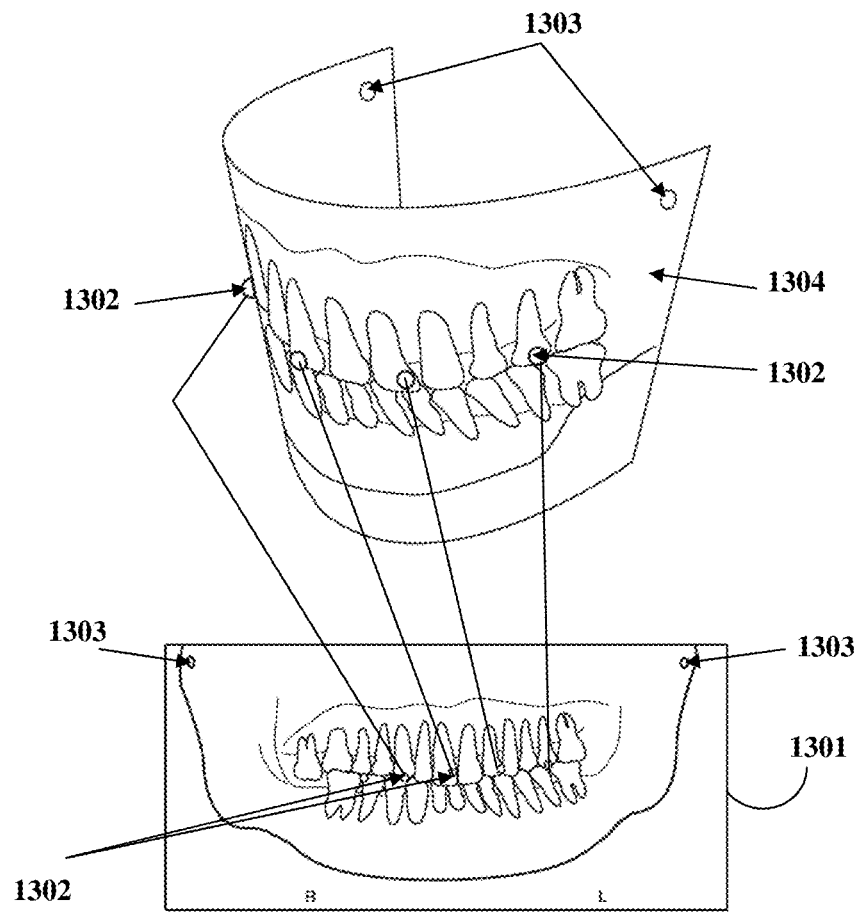
FIG. 13B exemplarily illustrates creation of a three-dimensional panoramic X-ray image of an upper jaw and a lower jaw of a patient's mouth with an inserted bite frame using the two-dimensional panoramic X-ray image shown in FIG. 13A.

FIG. 13B exemplarily illustrates creation of a three-dimensional (3D) panoramic X-ray image 1304 of the upper jaw 803 and the lower jaw 804 of a patient's mouth exemplarily illustrated in FIG. 8D, with an inserted bite frame 200 using the two-dimensional (2D) panoramic X-ray image 1301 shown in FIG. 13A. The panoramic machine 1102 exemplarily illustrated in FIG. 11, converts the 2D panoramic X-ray image 1301 to a 3D panoramic X-ray image 1304. The 3D panoramic X-ray image 1304 is created by curving the 2D panoramic X-ray image 1301 along a 3D focal plane of the panoramic machine 1102. The 3D panoramic X-ray image 1304 is registered to a 3D head surface image 1504 exemplarily illustrated in FIG. 15D, in which reference points 1303 provided by the external radio-opaque markers are recorded. The image processing system 1103 exemplarily illustrated in FIG. 11, matches the reference points 1302 and 1303 provided by the radio-opaque markers 201 and the external radio-opaque markers on the 3D panoramic X-ray image 1304 exemplarily illustrated in FIG. 13B, with the reference points 1302 provided by the radio-opaque markers 201 on the 3D scanned images of the bite impression registered in the bite registration material 601 exemplarily illustrated in FIGS. 6B-6D, for matching the 3D panoramic X-ray image 1304 with the 3D scanned image while determining a 3D relation between the patient's upper jaw 803 and lower jaw 804.

Figure 14A:
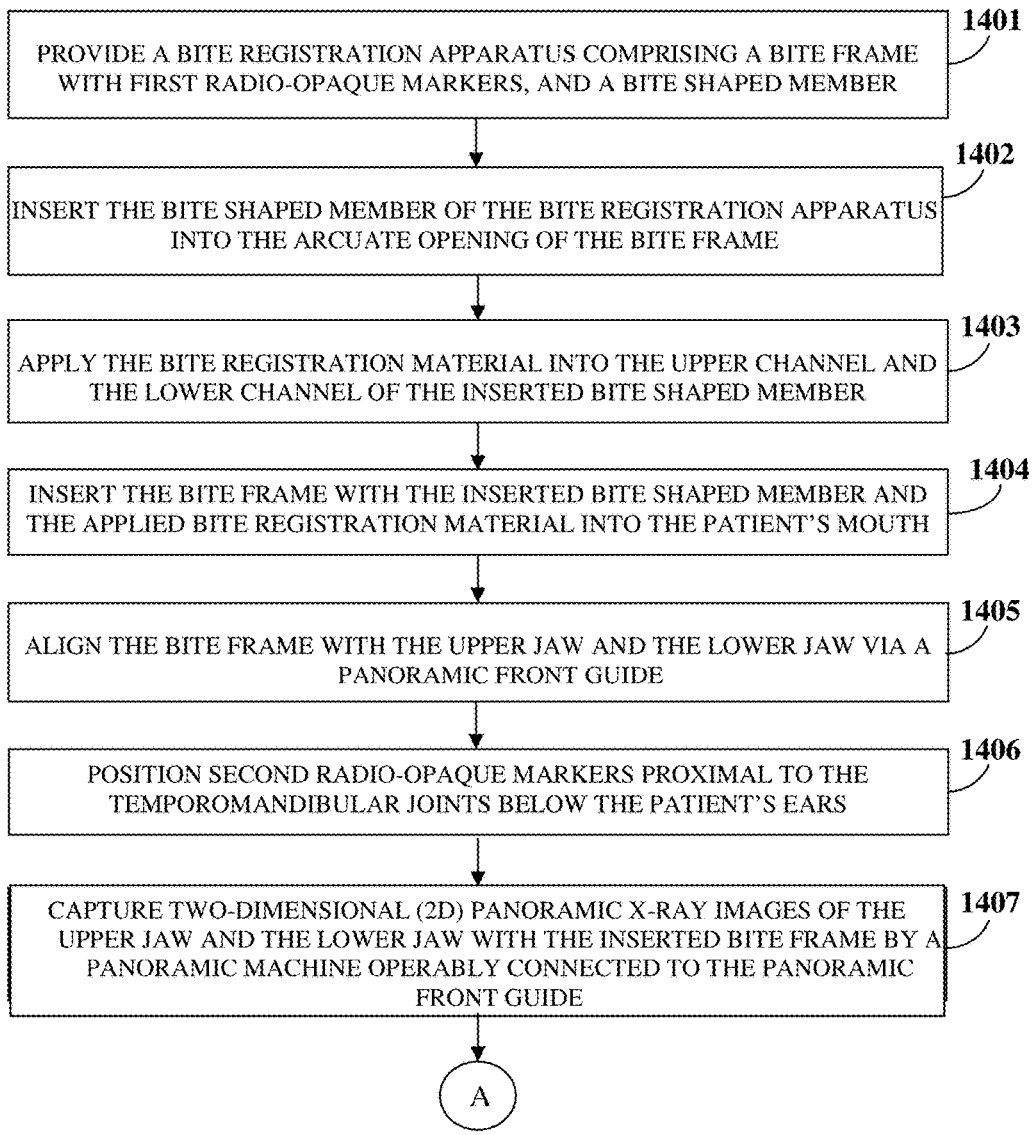
FIGS. 14A-14B illustrate a method for determining a three-dimensional relation between an upper jaw and a lower jaw with reference to temporomandibular joints of a patient.
Figure 14B:
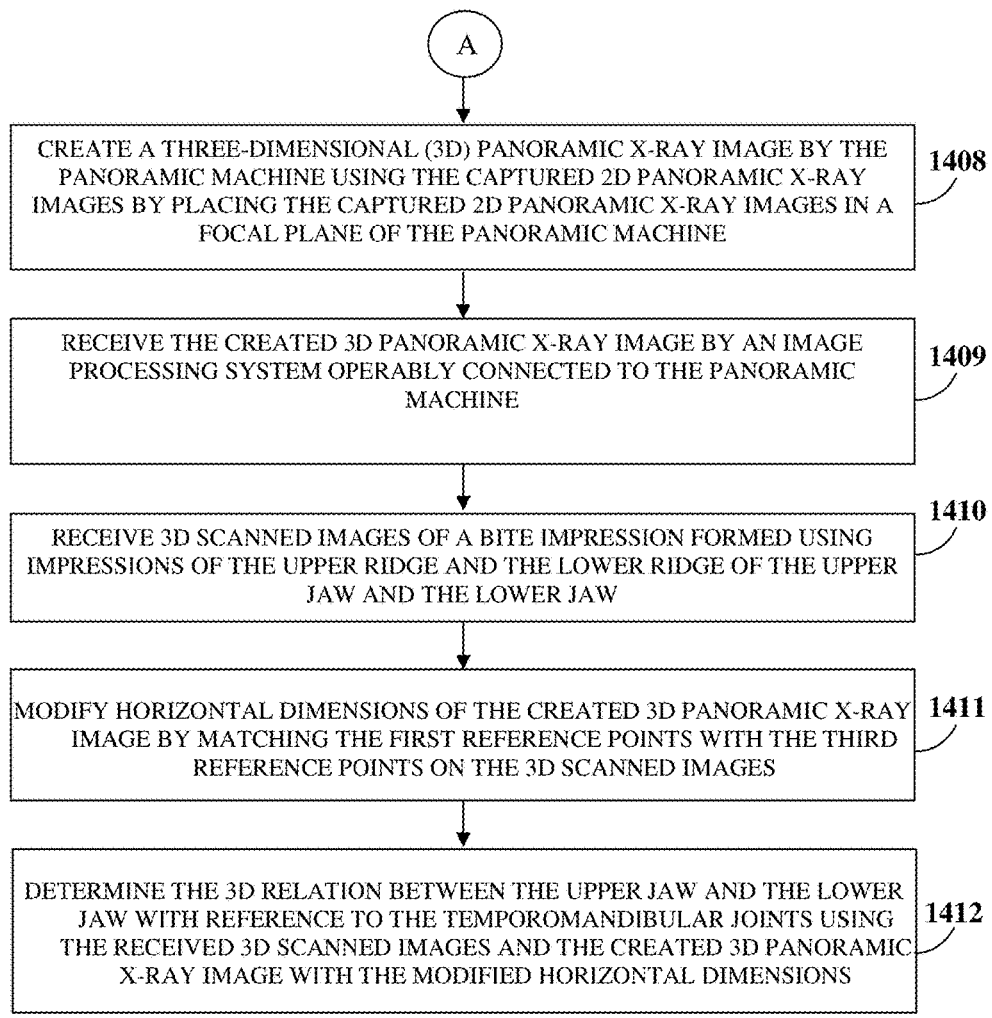

FIGS. 14A-14B illustrates a method for determining a three-dimensional (3D) relation between an upper jaw 803 and a lower jaw 804 exemplarily illustrated in FIG. 8D, with reference to temporomandibular joints (TMJs) of a patient. In the method disclosed herein, the bite registration apparatus 600 exemplarily illustrated in FIGS. 6A-6D, comprising the bite frame 200 exemplarily illustrated in FIGS. 2A-2B, and the bite shaped member 500, 700, or 900 exemplarily illustrated in FIGS. 5A-5D, FIGS. 7A-7E, and FIGS. 9A-9H, of one of multiple flexible geometric shapes is provided 1401. The bite frame 200 comprises first radio-opaque markers 201 exemplarily illustrated in FIGS. 2A-2B, configured to provide first reference points 1302 exemplarily illustrated in FIG. 13A, to positions of the upper jaw 803 and the lower jaw 804. The bite shaped member 500, 700, or 900 is inserted 1402 into an arcuate opening 103 of the bite frame 200 exemplarily illustrated in FIGS. 2A-2B. A bite registration material 601 exemplarily illustrated in FIGS. 6B-6D, is applied 1403 into the upper channel 502, 702, or 902 and the lower channel 504, 703, or 903 of the inserted bite shaped member 500, 700, or 900 exemplarily illustrated in FIGS. 5A-5D, FIGS. 7A-7E, and FIGS. 9A-9H respectively. In embodiment where the bite frame 300 exemplarily illustrated in FIG. 3, is used, the bite registration material 601 is applied on the mesh element 303 mounted in the wide arcuate opening 304 defined within the bite frame 300. In another example, the bite registration material 601 is injected into the upper channel 502, 702, or 902 and the lower channel 504, 703, or 903 of the bite shaped member 500, 700, or 900 accommodated in the narrow hollow arcuate opening 103 or 403 defined within the bite frame 100 or 400 exemplarily illustrated in FIGS. 1A-1D and FIG. 4 respectively.

The bite frame 200 with the inserted bite shaped member 500, 700, or 900 and the applied bite registration material 601 is inserted 1404 into the patient's mouth. After insertion of the bite frame 200 with the inserted bite shaped member 500, 700, or 900 and the applied bite registration material 601 into the patient's mouth, the bite frame 200 is aligned 1405 with the upper jaw 803 and the lower jaw 804 of the patient via the panoramic front guide 1101 exemplarily illustrated in FIG. 11. Second radio-opaque markers, for example, external radio-opaque markers (not shown) are positioned 1406 proximal to the temporomandibular joints below the patient's ears. The second radio-opaque markers are configured to provide second reference points 1303 to the temporomandibular joints. The patient is instructed to bite into the inserted bite shaped member 500, 700, or 900 to obtain the jaw relation. In the case of patients with natural dentition, the bite impression registered on the bite registration material 601 contains the 3D relation between the upper jaw 803 and the lower jaw 804. In the case of edentulous patients, the bite impression registered on the bite registration material 601 contains the 3D relation between the upper ridge 803a of the upper jaw 803 and the lower ridge 804a of the lower jaw 804 exemplarily illustrated in FIG. 8D. After the bite impression is manually registered, image capture and computer implemented image processing takes place to determine the three-dimensional (3D) relation between the upper jaw 803 and the lower jaw 804 of the patient. The registration of the bite impression enables a dental practitioner to optimally determine the 3D relation after image processing.

The panoramic machine 1102 operably connected to the panoramic front guide 1101 captures 1407 two-dimensional (2D) panoramic X-ray images 1301 exemplarily illustrated in FIG. 13A, of the upper jaw 803 and the lower jaw 804 with the inserted bite frame 200. For example, the panoramic machine 1102 captures the 2D panoramic X-ray images 1301 in and around a patient's mouth. The 2D panoramic X-ray image 1301 is a tomographic image of the upper jaw 803 and the lower jaw 804 along the focal plane of the panoramic machine 1102. The captured 2D panoramic X-ray images 1301 of the upper jaw 803 and the lower jaw 804 with the inserted bite frame 200 contain positions of the upper jaw 803 and the lower jaw 804 identified by the first reference points 1302 provided by the first radio-opaque markers 201 of the inserted bite frame 200, and locations of the temporomandibular joints identified by the second reference points 1303 provided by the second or external radio-opaque markers. The panoramic machine 1102 creates 1408 a three-dimensional (3D) panoramic X-ray image 1304 exemplarily illustrated in FIG. 13B, using the captured 2D panoramic X-ray images 1301 of the upper jaw 803 and the lower jaw 804 with the inserted bite frame 200, by placing the captured 2D panoramic X-ray images 1301 of the upper jaw 803 and the lower jaw 804 with the inserted bite frame 200 in a focal plane of the panoramic machine 1102. The 3D panoramic X-ray image 1304 is constructed by placing the 2D panoramic X-ray images 1301 back into the corresponding focal plane of the panoramic machine 1102. Since the focal plane is distributed unevenly along the horizontal dimension, the first reference points 1302 provided by the first radio-opaque markers 201 and the second reference points 1303 provided by the second or external radio-opaque markers are used to mark an accurate position of the horizontal position of the first radio-opaque markers 201, which facilitates the placement of the 2D panoramic X-ray images 1301 along the 3D focal plane.

The image processing system 1103 operably connected to the panoramic machine 1102 as exemplarily illustrated in FIG. 11, receives 1409 the created 3D panoramic X-ray image 1304 from the panoramic machine 1102. The image processing system 1103 receives 1410 3D scanned images 1601 exemplarily illustrated in FIG. 16, of the bite impression formed using the impression of the upper ridge 803a of the upper jaw 803 and the impression of the lower ridge 804a of the lower jaw 804 from the 3D scanner 1104 operably connected to the image processing system 1103 exemplarily illustrated in FIG. 11. The 3D scanned images 1601 comprise the positions of the upper jaw 803 and the lower jaw 804 identified by third reference points (not shown) provided by the first radio-opaque markers 201 of the inserted bite frame 200. The created 3D panoramic X-ray image 1304 and the 3D scanned images 1601 are overlapped in the same position in a 3D space. Since there are more than three radio-opaque markers 201 in the inserted bite frame 200, there will be only one way the 3D panoramic X-ray image 1304 and the 3D scanned images 1601 can be matched in the 3D space. The image processing system 1103 modifies 1411 horizontal dimensions of the created 3D panoramic X-ray image 1304 containing the positions of the upper jaw 803 and the lower jaw 804 and the locations of the temporomandibular joints, by matching the first reference points 1302 on the created 3D panoramic X-ray image 1304 with the third reference points on the 3D scanned images 1601 of the bite impression. The image processing system 1103 determines 1412 the 3D relation between the upper jaw 803 and the lower jaw 804 with reference to the temporomandibular joints of the patient using the received 3D scanned images 1601 and the created 3D panoramic X-ray image 1304 with the modified horizontal dimensions. The temporomandibular joint is a readily identifiable structure on the 3D panoramic X-ray image 1304. The horizontal distortion is minimal in the temporomandibular joint region of the 3D panoramic X-ray image 1304.

Since the horizontal dimensions of the created three-dimensional (3D) panoramic X-ray image 1304 are corrected in accordance with the radio-opaque markers 201, the created 3D panoramic X-ray image 1304 can be used to identify an accurate location of the upper jaw 803 and lower jaw 804 with reference to the temporomandibular joints (TMJs) identifiable in most 3D panoramic X-ray images 1304. Since the 3D scanned images 1601 contain the positions of the upper jaw 803 and the lower jaw 804 and the 3D panoramic X-ray image 1304 contains the 3D locations of the TMJs, the upper jaw 803 and the lower jaw 804 are related directly with the TMJs in a 3D space.

Figure 15A:
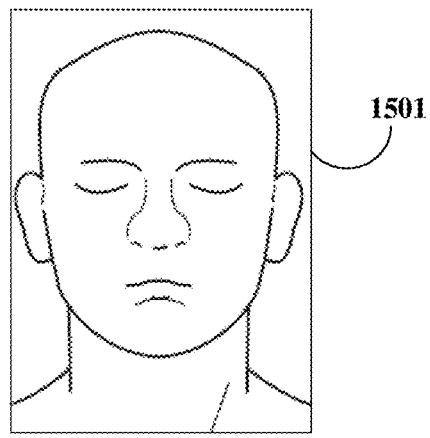
FIGS. 15A-15B exemplarily illustrate two-dimensional surface images of different views of a head structure of a patient.
Figure 15B:
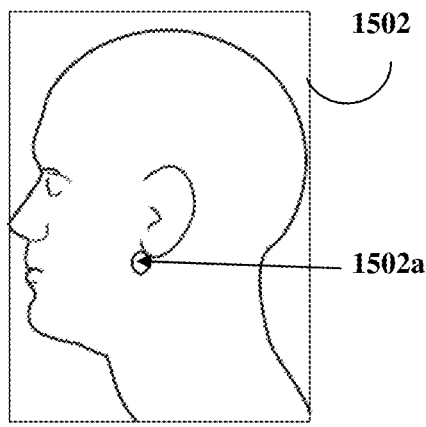

In an embodiment, the image processing system 1103 further receives 1309 two-dimensional (2D) surface images 1501 and 1502 exemplarily illustrated in FIGS. 15A-15B, of the patient's head structure, herein referred to as "2D head surface images". The 2D head surface images 1501 and 1502 comprise the locations of the temporomandibular joints identified by fourth reference points 1502a exemplarily illustrated in FIG. 15B, provided by the second radio-opaque markers. The image processing system 1103 constructs a three-dimensional head surface image 1504 comprising images of the upper jaw 803, the lower jaw 804, and the temporomandibular joints using the received 2D head surface images 1501 and 1502. The upper jaw bone and the lower jaw bone lie below the skin surface of the upper jaw 803 and the lower jaw 804. The temporomandibular joint lies below the ears. Therefore, the upper jaw 803, the lower jaw 804, and the temporomandibular joints can be found in the 3D space inside the 3D head surface image 1504. Since the upper lip and the lower lip can be found in the 3D head surface image 1504, the 3D relation of the upper lip 801 and the lower lip 802 and the upper jaw 803 and the lower jaw 804 exemplarily illustrated in FIG. 8D and FIG. 10C can also be found. The location of the temporomandibular joint is also finalized by matching the fourth reference points 1502a provided by the second or external radio-opaque markers on the 3D head surface image 1504. The image processing system 1103 matches the fourth reference points 1502a on the constructed 3D head surface image 1504 with the second reference points 1303 on the created panoramic X-ray image 1304 for checking and confirming the locations of the temporomandibular joints for verifying the 3D relation between the upper jaw 803 and the lower jaw 804 with reference to the temporomandibular joints.

Figure 15C:
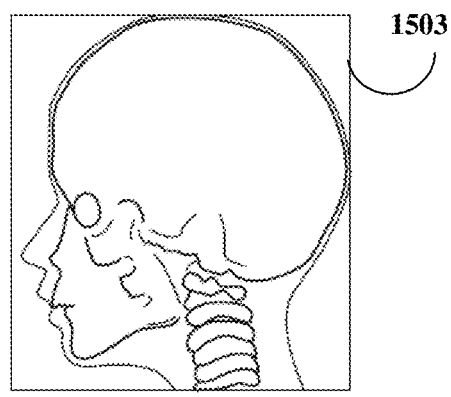
FIG. 15C exemplarily illustrates a cephalometric X-ray graph of a side view of the head structure of the patient.
Figure 15D:
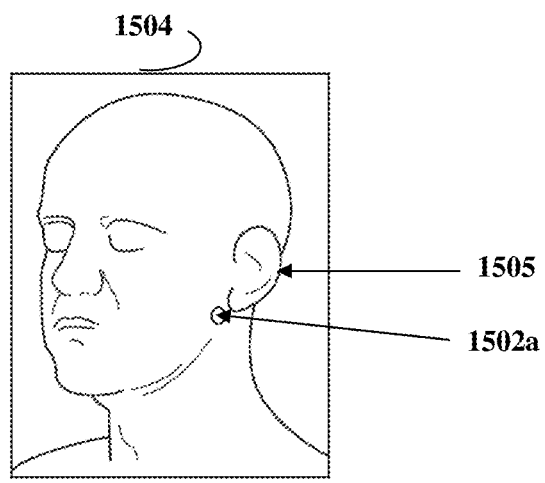
FIG. 15D exemplarily illustrates a three-dimensional head surface image constructed using the two-dimensional surface images shown in FIGS. 15A-15B and the cephalometric X-ray graph shown in FIG. 15C.

FIGS. 15A-15B exemplarily illustrate two-dimensional (2D) surface images 1501 and 1502 of different views of the head structure of a patient. FIG. 15A exemplarily illustrates a 2D surface image 1501 of a front view of the patient's head structure. FIG. 15B exemplarily illustrates a 2D surface image 1502 of a side view of the patient's head structure. FIG. 15C exemplarily illustrates a cephalometric X-ray graph 1503 of a side view of the patient's head structure. FIG. 15D exemplarily illustrates a three-dimensional (3D) head surface image 1504 constructed using the 2D surface images 1501 and 1502 shown in FIGS. 15A-15B, and the cephalometric X-ray graph 1503 shown in FIG. 15C. The image processing system 1103 exemplarily illustrated in FIG. 11, constructs the preliminary 3D surface image 1504 of the patient's head structure from the 2D surface images 1501 and 1502 exemplarily illustrated in FIGS. 15A-15B using a commercial software application, for example, Facegen® of Singular Inversions, Inc., or by the computer implemented method and system disclosed in the non-provisional patent application Ser. No. 12/701,622, now U.S. Pat. No. 8,244,017 titled "Constructing Three Dimensional Images Using Panoramic Images", filed in the United States Patent and Trademark Office on Feb. 8, 2010. The cephalometric X-ray graph 1503 assists in improving the accuracy of the 3D head surface image 1504. The 3D head surface image 1504 contains the locations of the temporomandibular joints (TMJs) below the ears 1505 as exemplarily illustrated in FIG. 15D. The bone structures such as the TMJs, the upper jaw 803, and the lower jaw 804 exemplarily illustrated in FIG. 8D and FIG. 10C can be identified inside the 3D head surface image 1504.

Figure 16:
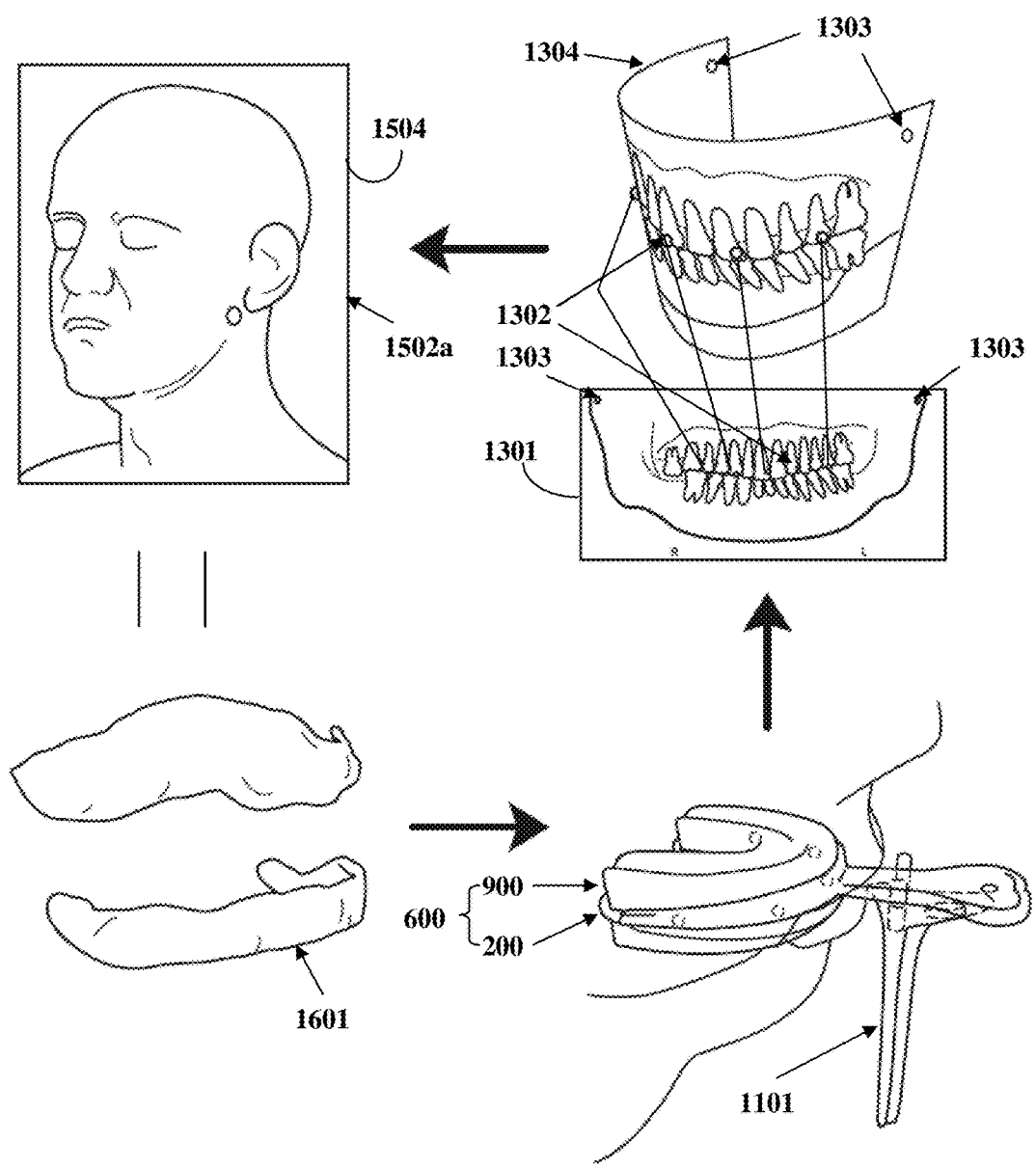
FIG. 16 exemplarily illustrates a sequence of procedural steps for determining a three-dimensional relation between an upper jaw and a lower jaw with reference to temporomandibular joints of a patient.

FIG. 16 exemplarily illustrates a sequence of procedural steps for determining a three-dimensional (3D) relation between the upper jaw 803 and the lower jaw 804 exemplarily illustrated in FIG. 8D, with reference to temporomandibular joints (TMJs) of the patient. A 3D scanned image 1601 of the bite impression and a 3D panoramic X-ray image 1304 of the upper jaw 803 and the lower jaw 804 created using the 2D panoramic X-ray images 1301 of the bite frame 200 with the bite shaped member 900 inserted in the patient's mouth are registered using reference points 1302 provided by the radio-opaque markers 201 exemplarily illustrated in FIGS. 2A-2B, and the external radio-opaque markers. The 3D head surface image 1504 is then registered with the 3D panoramic X-ray image 1304 by matching the locations of the temporomandibular joints and the upper jaw 803 and the lower jaw 804 inside the 3D head surface image 1504. The 3D panoramic X-ray image 1304 of the upper jaw 803 and the lower jaw 804 can be registered precisely within the 3D head surface image 1504. A dental prosthesis and appliance can be designed optimally with reference to the temporomandibular joints to achieve optimal chewing function and achieve optimal esthetics appearance with reference to the upper lip 801 and lower lip 802 exemplarily illustrated in FIG. 8D and FIG. 10C.

In an embodiment, the bite frame 100, 200, 300, or 400 with the bite shaped member 500, 700, or 900 can be used for determining a 3D relation between the upper jaw 803 and the lower jaw 804 of a patient with full dentition, for example, a patient who needs orthodontic treatment such as in pediatric dentistry, restorative dentistry, in an airway management appliance, etc. The bite frame 100, 200, 300, or 400 with the bite shaped member 500, 700, or 900 can be used to register the upper teeth and the lower teeth with the temporomandibular joints (TMJs) and 3D head surface image 1504. The registration facilitates an understanding of the development of the upper jaw 803 and the lower jaw 804 in relation with the upper teeth and lower teeth and helps a dentist design an optimal orthodontic appliance to correct the jaw relation and the teeth alignment without causing problems to the TMJs.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention in its aspects.

We claim:

1. A bite registration apparatus for enabling determination of a three-dimensional relation between an upper jaw and a lower jaw, said bite registration apparatus comprising:
   a bite frame comprising:
      a handle; and
      an arcuate frame element rigidly connected to an upper end of said handle, said arcuate frame element configured to define a generally narrow hollow arcuate opening, said generally narrow hollow arcuate opening configured to accommodate a bite shaped member; and
   said bite shaped member configured to be accommodated within said generally narrow hollow arcuate opening of said bite frame, said bite shaped member comprising:
      a body structure having an upper surface and a lower surface separated by a mid-section, said upper surface of said body structure configured to conform to said upper jaw, and said lower surface of said body structure configured to conform to said lower jaw;
      an upper channel of a configurable shape defined on said upper surface of said body structure, said upper channel configured to receive a bite registration material and engage an upper ridge of said upper jaw to register an impression of said upper ridge of said upper jaw;
      a lower channel of a configurable shape defined on said lower surface of said body structure, said lower channel configured to receive said bite registration material and engage a lower ridge of said lower jaw to register an impression of said lower ridge of said lower jaw, wherein said registration of said impression of said upper ridge of said upper jaw and said impression of said lower ridge of said lower jaw that constitute a bite impression enables said determination of said three-dimensional relation between said upper jaw and said lower jaw;
      upper windows positioned along said upper channel on said upper surface of said body structure, and lower windows positioned along said lower channel on said lower surface of said body structure, said upper windows and said lower windows separated by a space within said bite shaped member, said space configured to receive said bite registration material from said upper channel and said lower channel through said upper windows and said lower windows respectively;
      said upper windows, in fluid communication with said lower windows, configured to allow flow of said received bite registration material from said upper channel to said lower channel to register a vertical distance between said upper ridge of said upper jaw and said lower ridge of said lower jaw for said determination of said three-dimensional relation between said upper jaw and said lower jaw; and
      said bite shaped member formed of a flexible porous material configurable for changing a shape and a form of said bite shaped member for folding and said accommodation of said bite shaped member into said generally narrow hollow arcuate opening of said arcuate frame element of said bite frame, wherein said flexible porous material is configured to absorb said bite registration material.

2. A bite registration apparatus for enabling determination of a three-dimensional relation between an upper jaw and a lower jaw, said bite registration apparatus comprising:
   a bite frame comprising:
      a handle; and
      an arcuate frame element rigidly connected to an upper end of said handle, said arcuate frame element configured to define a generally narrow hollow arcuate opening, said generally narrow hollow arcuate opening configured to accommodate a bite shaped member; and
   said bite shaped member configured to be accommodated within said generally narrow hollow arcuate opening of said bite frame, said bite shaped member comprising:
      a body structure having an upper surface and a lower surface separated by a mid-section, said upper surface of said body structure configured to conform to said upper jaw, and said lower surface of said body structure configured to conform to said lower jaw;
      an upper channel of a configurable shape defined on said upper surface of said body structure, said upper channel configured to receive a bite registration material and engage an upper ridge of said upper jaw to register an impression of said upper ridge of said upper jaw;
      a lower channel of a configurable shape defined on said lower surface of said body structure, said lower channel configured to receive said bite registration material and engage a lower ridge of said lower jaw to register an impression of said lower ridge of said lower jaw, wherein said registration of said impression of said upper ridge of said upper jaw and said impression of said lower ridge of said lower jaw that constitute a bite impression enables said determination of said three-dimensional relation between said upper jaw and said lower jaw;

upper windows positioned along said upper channel on said upper surface of said body structure, and lower windows positioned along said lower channel on said lower surface of said body structure, said upper windows and said lower windows separated by a space within said bite shaped member, said space configured to receive said bite registration material from said upper channel and said lower channel through said upper windows and said lower windows respectively;

said upper windows, in fluid communication with said lower windows, configured to allow flow of said received bite registration material from said upper channel to said lower channel to register a vertical distance between said upper ridge of said upper jaw and said lower ridge of said lower jaw for said determination of said three-dimensional relation between said upper jaw and said lower jaw; and said bite shaped member formed of a flexible porous material with a generally low pore per inch value to allow enhanced penetration of said bite registration material into said upper channel and said lower channel of said bite shaped member for said registration of said impression of said upper ridge of said upper jaw and said registration of said impression of said lower ridge of said lower jaw.

3. A bite shaped member configured to be accommodated within a bite frame for enabling determination of a three-dimensional relation between an upper jaw and a lower jaw, said bite shaped member comprising:

a body structure having an upper surface and a lower surface separated by a mid-section, said upper surface of said body structure configured to conform to said upper jaw, and said lower surface of said body structure configured to conform to said lower jaw;

an upper channel of a configurable shape defined on said upper surface of said body structure, said upper channel configured to receive a bite registration material and engage an upper ridge of said upper jaw to register an impression of said upper ridge of said upper jaw;

a lower channel of a configurable shape defined on said lower surface of said body structure, said lower channel configured to receive said bite registration material and engage a lower ridge of said lower jaw to register an impression of said lower ridge of said lower jaw, wherein said registration of said impression of said upper ridge of said upper jaw and said impression of said lower ridge of said lower jaw that constitute a bite impression enables said determination of said three-dimensional relation between said upper jaw and said lower jaw;

upper windows positioned along said upper channel on said upper surface of said body structure, and lower windows positioned along said lower channel on said lower surface of said body structure, said upper windows and said lower windows separated by a space within said bite shaped member, said space configured to receive said bite registration material from said upper channel and said lower channel through said upper windows and said lower windows respectively;

said upper windows, in fluid communication with said lower windows, configured to allow flow of said received bite registration material from said upper channel to said lower channel to register a vertical distance between said upper ridge of said upper jaw and said lower ridge of said lower jaw for said determination of said three-dimensional relation between said upper jaw and said lower jaw; and said bite shaped member formed of a flexible porous material configurable for changing shape and form for folding and accommodating said bite shaped member into a generally narrow hollow arcuate opening of an arcuate frame element of said bite frame, wherein said flexible porous material is configured to absorb said bite registration material.

4. A bite shaped member configured to be accommodated within a bite frame for enabling determination of a three-dimensional relation between an upper jaw and a lower jaw, said bite shaped member comprising:

a body structure having an upper surface and a lower surface separated by a mid-section, said upper surface of said body structure configured to conform to said upper jaw, and said lower surface of said body structure configured to conform to said lower jaw;

an upper channel of a configurable shape defined on said upper surface of said body structure, said upper channel configured to receive a bite registration material and engage an upper ridge of said upper jaw to register an impression of said upper ridge of said upper jaw;

a lower channel of a configurable shape defined on said lower surface of said body structure, said lower channel configured to receive said bite registration material and engage a lower ridge of said lower jaw to register an impression of said lower ridge of said lower jaw, wherein said registration of said impression of said upper ridge of said upper jaw and said impression of said lower ridge of said lower jaw that constitute a bite impression enables said determination of said three-dimensional relation between said upper jaw and said lower jaw;

upper windows positioned along said upper channel on said upper surface of said body structure, and lower windows positioned along said lower channel on said lower surface of said body structure, said upper windows and said lower windows separated by a space within said bite shaped member, said space configured to receive said bite registration material from said upper channel and said lower channel through said upper windows and said lower windows respectively;

said upper windows, in fluid communication with said lower windows, configured to allow flow of said received bite registration material from said upper channel to said lower channel to register a vertical distance between said upper ridge of said upper jaw and said lower ridge of said lower jaw for said determination of said three-dimensional relation between said upper jaw and said lower jaw; and said bite shaped member formed of a flexible porous material with a generally low pore per inch value to allow enhanced penetration of said bite registration material into said upper channel and said lower channel of said bite shaped member for said registration of said impression of said upper ridge of said upper jaw and said registration of said impression of said lower ridge of said lower jaw.

5. A method for determining a three-dimensional relation between an upper jaw and a lower jaw with reference to temporomandibular joints of a patient, said method comprising:

providing a bite registration apparatus comprising:
   a bite frame comprising:
      a handle;

an arcuate frame element rigidly connected to an upper end of said handle, said arcuate frame element configured to define a generally arcuate opening; and first radio-opaque markers positioned at predetermined locations along an inner rim of said arcuate frame element, wherein said first radio-opaque markers are configured to provide first reference points to positions of said upper jaw and said lower jaw; and a bite shaped member of one of a plurality of flexible geometric shapes configured to be accommodated within said generally arcuate opening of said bite frame, said bite shaped member comprising:

a body structure having an upper surface and a lower surface separated by a mid-section, said upper surface of said body structure configured to conform to said upper jaw, and said lower surface of said body structure configured to conform to said lower jaw;

an upper channel of a configurable shape defined on said upper surface of said body structure, said upper channel configured to receive a bite registration material and engage an upper ridge of said upper jaw to register an impression of said upper ridge of said upper jaw;

a lower channel of a configurable shape defined on said lower surface of said body structure, said lower channel configured to receive said bite registration material and engage a lower ridge of said lower jaw to register an impression of said lower ridge of said lower jaw, wherein said impression of said upper ridge of said upper jaw and said impression of said lower ridge of said lower jaw constitute a bite impression;

upper windows positioned along said upper channel on said upper surface of said body structure, and lower windows positioned along said lower channel on said lower surface of said body structure, said upper windows and said lower windows separated by a space within said bite shaped member, said space configured to receive said bite registration material from said upper channel and said lower channel through said upper windows and said lower windows respectively; and said upper windows, in fluid communication with said lower windows, configured to allow flow of said received bite registration material from said upper channel to said lower channel to register a vertical distance between said upper ridge of said upper jaw and said lower ridge of said lower jaw;

inserting said bite shaped member of said bite registration apparatus into said generally arcuate opening of said bite frame of said bite registration apparatus;

applying said bite registration material into said upper channel and said lower channel of said inserted bite shaped member;

inserting said bite frame with said inserted bite shaped member and said applied bite registration material into a mouth of said patient, and aligning said bite frame with said upper jaw and said lower jaw via a panoramic front guide;

positioning second radio-opaque markers proximal to said temporomandibular joints below ears of said patient, wherein said second radio-opaque markers are configured to provide second reference points to said temporomandibular joints;

capturing two-dimensional panoramic X-ray images of said upper jaw and said lower jaw with said inserted bite frame by a panoramic machine operably connected to said panoramic front guide, wherein said captured two-dimensional panoramic X-ray images of said upper jaw and said lower jaw with said inserted bite frame contain said positions of said upper jaw and said lower jaw identified by said first reference points provided by said first radio-opaque markers of said inserted bite frame, and locations of said temporomandibular joints identified by said second reference points provided by said second radio-opaque markers;

creating a three-dimensional panoramic X-ray image by said panoramic machine using said captured two-dimensional panoramic X-ray images of said upper jaw and said lower jaw with said inserted bite frame, by placing said captured two-dimensional panoramic X-ray images of said upper jaw and said lower jaw with said inserted bite frame in a focal plane of said panoramic machine;

receiving said created three-dimensional panoramic X-ray image by an image processing system operably connected to said panoramic machine, said image processing system comprising at least one processor configured to process said created three-dimensional panoramic X-ray image;

receiving three-dimensional scanned images of said bite impression formed using said impression of said upper ridge of said upper jaw and said impression of said lower ridge of said lower jaw, by said image processing system from a three-dimensional scanner operably connected to said image processing system, wherein said received three-dimensional scanned images comprise said positions of said upper jaw and said lower jaw identified by third reference points provided by said first radio-opaque markers of said inserted bite frame;

modifying horizontal dimensions of said created three-dimensional panoramic X-ray image containing said positions of said upper jaw and said lower jaw and said locations of said temporomandibular joints by said image processing system, by matching said first reference points on said created three-dimensional panoramic X-ray image with said third reference points on said three-dimensional scanned images of said bite impression; and determining said three-dimensional relation between said upper jaw and said lower jaw with reference to said temporomandibular joints of said patient by said image processing system using said received three-dimensional scanned images and said created three-dimensional panoramic X-ray image with said modified horizontal dimensions.

6. The method of claim 5, further comprising:

receiving two-dimensional surface images of a head structure of said patient by said image processing system, wherein said received two-dimensional surface images comprise said locations of said temporomandibular joints identified by fourth reference points provided by said second radio-opaque markers;

constructing a three-dimensional head surface image comprising images of said upper jaw, said lower jaw, and said temporomandibular joints by said image processing system using said received two-dimensional surface images of said head structure; and matching said fourth reference points on said constructed three-dimensional head surface image with said second reference points on said created three-dimensional panoramic X-ray image for checking and confirming said locations of said temporomandibular joints for verifying said three-dimensional relation between said upper jaw and said lower jaw with reference to said temporomandibular joints.

* * * * *